US009801955B2

(12) United States Patent
Thompson et al.

(10) Patent No.: US 9,801,955 B2
(45) Date of Patent: Oct. 31, 2017

(54) METHODS AND COMPOSITIONS FOR DETECTING DRUSEN AND PREDICTING AGE-RELATED MACULAR DEGENERATION

(71) Applicants: University of Maryland, Baltimore, Baltimore, MD (US); UCL Business PLC, London (GB)

(72) Inventors: Richard Thompson, Baltimore, MD (US); Imre Lengyel, London (GB)

(73) Assignee: University of Maryland, Baltimore, Baltimore, MD (US)

( * ) Notice: Subject to any disclaimer, the term of this patent is extended or adjusted under 35 U.S.C. 154(b) by 260 days.

(21) Appl. No.: 14/424,904

(22) PCT Filed: Aug. 30, 2013

(86) PCT No.: PCT/US2013/057661
§ 371 (c)(1),
(2) Date: Feb. 27, 2015

(87) PCT Pub. No.: WO2014/036483
PCT Pub. Date: Mar. 6, 2014

(65) Prior Publication Data
US 2015/0231279 A1  Aug. 20, 2015

Related U.S. Application Data

(60) Provisional application No. 61/695,434, filed on Aug. 31, 2012.

(30) Foreign Application Priority Data

Apr. 11, 2013  (GB) .................................. 1306627.9

(51) Int. Cl.
*A61K 49/00* (2006.01)
*G01N 33/58* (2006.01)
*A61K 51/04* (2006.01)
*G01N 33/84* (2006.01)
*A61K 9/00* (2006.01)

(52) U.S. Cl.
CPC ........ *A61K 49/0017* (2013.01); *A61K 9/0048* (2013.01); *A61K 49/0004* (2013.01); *A61K 51/04* (2013.01); *G01N 33/582* (2013.01); *G01N 33/84* (2013.01)

(58) Field of Classification Search
None
See application file for complete search history.

(56) References Cited

U.S. PATENT DOCUMENTS

2009/0123383 A1  5/2009  Frangioni

FOREIGN PATENT DOCUMENTS

| WO | 9517673 A1 | 6/1995 | |
| WO | 00/52479 | 9/2000 | |
| WO | 02/38190 A2 | 5/2002 | |
| WO | WO 0238190 A2 * | 5/2002 | ......... A61K 49/0032 |
| WO | 2006047475 A2 | 5/2006 | |
| WO | 108704 A1 | 9/2009 | |
| WO | 2010/116132 A2 | 10/2010 | |

OTHER PUBLICATIONS

Lim, L. S., Mitchell, P., Seddon, J. M., Holz, F. G. and Wong, T. Y. Age-related macular degeneration. The Lancet 379, 1728-1738, doi:http://dx.doi.org/10.1016/S0140-6736(12)60282-7 (2012).
Sarks, S. H. Ageing and degeneration in the macular region: a clinico-pathological study. The British journal ophthalmology 60, 324-341 (1976).
Sarks, S. H., Arnold, J. J., Killingsworth, M. C. and Sarks, J. P. Early drusen formation in the normal and aging eye and their relation to age related maculopathy: a clinicopathological study. The British journal of ophthalmology 83, 358-368 (1999).
Pauleikhoff, D., Harper, C. A., Marshall, J. and Bird, A. C. Aging changes in Bruch's membrane. A histochemical and morphologic study. Ophthalmology 97, 171-178 (1990).
Pauleikhoff, D., Barondes, M. J., Minassian, D., Chisholm, I. H. and Bird, A. C. Drusen as risk factors in age-related macular disease. American journal of ophthalmology 109, 38-43 (1990).
Lengyel, I. et al. Association of drusen deposition with choroidal intercapillary pillars in the aging human eye. Invest Ophthalmol Vis Sci 45, 2886-2892 (2004).
Giachelli, C. M. Ectopic calcification: gathering hard facts about soft tissue mineralization. The American journal of pathology 154, 671-675, doi:10.1016/S0002-9440(10)65313-8 (1999).
Davis, W. L., Jones, R. G. and Hagler, H. K. An electron microscopic histochemical and analytical X-ray microprobe study of calcification in Bruch's membrane from human eyes. The journal of histochemistry and cytochemistry: official journal of the Histochemistry Society 29, 601-608 (1981).
Vogt, S. D. et al. Retinal pigment epithelial expression of complement regulator CD46 is altered early in the course of geographic atrophy. Experimental eye research 93, 413-423, doi:10.1016/j.exer.2011.06.002 (2011).
Raggatt, L. J. & Partridge, N. C. Cellular and molecular mechanisms of bone remodeling. The Journal of biological chemistry 285, 25103-25108, doi:10.1074/jbc.R109.041087 (2010).
Skinner, H. C. and Nalbandian, J. Tetracyclines and mineralized tissues: review and perspectives. Yale J Biol Med 48, 377-397 (1975).

(Continued)

*Primary Examiner* — Michael G Hartley
*Assistant Examiner* — Jennifer Lamberski
(74) *Attorney, Agent, or Firm* — Stites & Harbison, PLLC; Mandy Wilson Decker

(57) ABSTRACT

Labels and methods are provided for detecting deposits, including drusen, sub-retinal deposits, basal laminar and linear deposits, and the like. The labels can detect the presence, progression, or regression of hydroxyapatite, which can be indicative of the presence or the potential to develop such deposits. The labels can include a conjugate comprising a hydroxyapatite binding moiety and a label moiety, which can provide a detectable signal upon binding of the conjugate to hydroxyapatite. The labels and methods can be utilized to detect deposits in eye tissue, such as the retina, brain tissue, or the like. Methods are also provided for utilizing the present labels to predict or diagnose a neurodegenerative disease, including age-related macular degeneration. Accordingly, some methods can predict or diagnose age-related macular degeneration, including early signs or advanced forms thereof, based on the presence of hydroxyapatite in a tissue sample obtained from a subject.

21 Claims, 7 Drawing Sheets

(56) References Cited

OTHER PUBLICATIONS

Kovar, J. L. et al. Near-infrared-labeled tetracycline derivative is an effective marker of bone deposition in mice. Anal Biochem 416, 167-173, doi:10.1016/j.ab.2011.05.011 (2011).
Vilmann, H. The in vivo staining of bone with alizarin red S. J Anat 105, 533-545 (1969).
Rahn, B. A. and Perren, S. M. Xylenol orange, a fluorochrome useful in polychrome sequential labeling of calcifying tissues. Stain Technol 46, 125-129 (1971).
Mullins, R. F., et al. Drusen associated with aging and age-related macular degeneration contain proteins common to extracellular deposits associated with atherosclerosis, elastosis, amyloidosis, and dense deposit disease. Faseb J 14, 835-846 (2000).Mullins, R. F., Russell, S. R., Anderson, D. H. and Hageman, G. S. Drusen associated with aging and age-related macular degeneration contain proteins common to extracellular deposits associated with atherosclerosis, elastosis, amyloidosis, and dense deposit disease. Faseb J 14, 835-846 (2000).
Hageman, G. S. and Mullins, R. F. Molecular composition of drusen as related to substructural phenotype. Mol Vis 5, 28 (1999).
Russell, S. R., et al. Location, substructure, and composition of basal laminar drusen compared with drusen associated with aging and age-related macular degeneration. American journal of ophthalmology 129, 205-214 (2000). Russell, S. R., Mullins, R. F., Schneider, B. L. and Hageman, G. S. Location, substructure, and composition of basal laminar drusen compared with drusen associated with aging and age-related macular degeneration. American journal of ophthalmology 129, 205-214 (2000).
Curcio, C. A., Millican, C. L., Bailey, T. and Kruth, H. S. Accumulation of cholesterol with age in human Bruch's membrane. Invest Ophthalmol Vis Sci 42, 265-274 (2001).
Raggio, C. L., Boyan, B. D. and Boskey, A. L. In vivo hydroxyapatite formation induced by lipids. J Bone Miner Res 1, 409-415, doi:10.1002/jbmr.5650010505 (1986).
Pecorella, I., Ciardi, A., Scardino, A., Marasco, A. and Di Tondo, U. A scanning transmission microscopy and energy-dispersive X-ray microanalysis of idiopathic ocular calcification and oxalosis in AIDS patients. Ultrastruct Pathol 23, 223-231 (1999).
Spraul, C. W. and Grossniklaus, H. E. Characteristics of Drusen and Bruch's membrane in postmortem eyes with age-related macular degeneration. Archives of ophthalmology 115, 267-273 (1997).
Ulshafer, R. J., Allen, C. B., Nicolaissen, B., Jr. and Rubin, M. L. Scanning electron microscopy of human drusen. Investigative ophthalmology & visual science 28, 683-689 (1987).
Ulshafer, R. J., Allen, C. B. and Rubin, M. L. Distributions of elements in the human retinal pigment epithelium. Archives of ophthalmology 108, 113-117 (1990).
Van Der Schaft, T. L., De Bruijn, W. C., Mooy, C. M., Ketelaars, D. A. and De Jong, P. T. Element analysis of the early stages of age-related macular degeneration. Archives of ophthalmology 110, 389-394 (1992).

\* cited by examiner

ALIZARIN RED S

TETRACYCLINE

XYLENOL ORANGE

US 9,801,955 B2

METHODS AND COMPOSITIONS FOR DETECTING DRUSEN AND PREDICTING AGE-RELATED MACULAR DEGENERATION

TECHNICAL FIELD

The presently-disclosed subject matter relates to a composition for use in diagnosing neurodegenerative diseases such as age related macular degeneration (AMD), Alzheimer's disease (AD), and related conditions, and particularly those in which deposits are formed between the retinal pigment epithelium and the Bruch's membrane (BM), or to identifying a predisposition to, or likelihood of developing such neurodegenerative diseases. In particular, the presently-disclosed subject matter relates to a composition for and a method of identifying the presence of drusen or other sub-retinal deposits or similar deposits other tissues, and for targeting agents at the deposits.

INTRODUCTION

Many neurodegenerative disorders are characterized by the accumulation of intracellular or extracellular protein aggregates that increase with advancing age. In the eye Bruch's membrane (BM), which is interposed between the retinal pigment epithelium (RPE) and choroid, becomes thickened with age. The thickening is associated with accumulation of deposits, termed generally as sub-RPE deposits, that may be focal (recognized clinically as sub-retinal deposits or drusen) or diffuse (basal laminar or linear deposits, depending on whether they are present internal or external to the RPE basement membrane). The process occurs maximally in the macula, the locus of highest resolution vision, and is integral to the pathogenesis of age-related macular degeneration (AMD) but remains poorly understood. AMD is the most prevalent cause of blindness in the elderly in the developed world: for instance, over eight million Americans suffer from intermediate or advanced AMD.

The formation of the lipid- and protein-rich sub-RPE deposits, which are found both in the central and the peripheral retina, is likely to be important in the development of AMD. These deposits contain several different proteins derived from sources both in the retina and the serum, notably including beta-amyloid, complement factor H, serum albumin, vitronectin, apolipoprotein E, and crystallins; some of these proteins are known to avidly bind metal ions such as zinc.

The presence of sub-retinal deposits is indicative of a number of degenerative diseases. It would be advantageous to be able to easily identify sub-retinal deposits, especially at an early stage, to assist with the diagnosis of such conditions. In particular, there remains a need for compounds and methods that can accurately detect degenerative diseases, including age-related macular degeneration at early stages of the disease, thereby providing an opportunity for superior treatment outcomes.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a hydroxyapatite (HAP) label for use in the identification or labelling of drusen or other similar deposits. In some embodiments the HAP label comprises a HAP binding moiety selected from the group consisting of tetracycline derivatives, xylenol orange, alizarin, calcein, phosphonates, bis-phosphonates, pamidronate, bis-iminodiacetates, HAP-binding peptides, and combinations thereof. In specific embodiments the label is for use in the identification of drusen or other similar deposits, and especially sub-retinal deposits such as basal laminar or linear deposits, and comprises an HAP binding moiety selected from tetracycline derivatives, xylenol orange, alizarin, calcein, phosphonates, pamidronate, bis-iminodiacetates, HAP-binding peptides, and combinations thereof.

In this regard, certain embodied labels can produce a signal which can be detected from outside a tissue in which the drusen or other similar deposits are found. In some embodiments the HAP-binding moiety is itself capable of producing a signal which may be detected from outside the tissue in which the deposit is found. Also, in some embodiments the label comprises a signal generating moiety. The signal generating moiety can be a visualizable or optical label moiety, which can be detectable by optical methods selected from fluorescence, fluorescence lifetime, fluorescence lifetime imaging, fluorescence polarization or anisotropy, chemiluminescence, phosphorescence, bioluminescence, Raman scattering, absorption, polarimetry, second harmonic generation, and combinations thereof. For instance, the signal generating moiety can be selected from Dyomics dye DY-776, Dyomics Dye 781, Licor IRDye 680, IRDye 800, and PAM-78. Thus, some of the present labels can comprise an HAP binding moiety, which may or may not be capable of producing a detectable signal, conjugated to a signal generating moiety which is capable of producing a detectable signal. Certain labels can be configured such that the label exhibits a change in detectable signal upon binding to HAP.

With regard to the signal generating moiety, in some embodiments the signal generating moiety can comprise a fluorescent label moiety including any suitable emission or excitation spectrum. In some preferred embodiments the emission spectrum is in the visible range, near infrared range, infrared range, or combinations thereof. In other embodiments the emission spectrum may be in the ultraviolet and/or blue region (e.g., peak wavelength of about 10 to about 450 nm). In some embodiments the emission wavelength of a signal generating moiety is selected to take into account potential interfering fluorescence, absorption, and/or scattering. For example, in certain implementations shorter wavelength radiation (e.g., ultraviolet, blue, etc.) experiences relatively greater amounts of scattering and interfering fluorescence. Thus. in some preferred embodiments, the emission spectrum can include a peak wavelength of at least about 450 nm, of less than about 1800 nm, or of between about 450 nm and about 1800 nm. In some embodiments the label comprises, alternatively or in addition to other signal generating moieties, a non-optical label. The non-optical label can comprise $^{99m}$Tc, a lanthanide complex, or a combination thereof. For example, the non-optical label can be a radionuclide such as $^{18}F$, a complex of a radionuclide such as $^{99m}Tc$, a complex of a paramagnetic ion such as Gadolinium, or a combination thereof. A non-optical label may be configured to be detected by positron emission tomography (PET), single photon emission computed tomography (SPECT), (nuclear) magnetic resonance imaging (N)MRI, or electron spin resonance, for example.

Furthermore, the identification or labelling of drusen or similar deposits using the embodied labels can be used in diagnosing or predicting the likelihood of having or developing age-related macular degeneration, or assessing the status of age-related macular degeneration in a subject, the age-related macular degeneration being associated with the presence of drusen or other similar deposits. In some embodiments the drusen or other similar deposits are in the eye, are sub-retinal deposits, are basal laminar deposits, basal linear deposits, are in the brain, or the like.

The presently-disclosed subject matter further includes methods for predicting or diagnosing age-related macular degeneration or detecting deposits. In some embodiments the methods comprise administering to a subject a HAP label or a HAP label compound as described herein, obtaining a profile of HAP deposits in the subject, and using the obtained profile to diagnose or predict age-related macular degeneration, detect deposits, or a combination thereof. In other embodiments the method comprises administering to a subject a HAP label compound comprising an HAP binding moiety and a label moiety, obtaining a profile of HAP deposits in the subject, and then using the obtained profile to predict or diagnose age-related macular degeneration, detect deposits, or a combination thereof. The HAP deposits can be in the eye of the subject.

In some embodiments, obtaining a profile of deposits in the subject comprises scanning the subject for labeled deposits. The deposits themselves can include drusen, sub-retinal deposits, basal laminar or linear deposits, or combinations thereof. Furthermore, the scanning of the subject for labeled deposits can comprise scanning the retina of the subject or scanning the brain of the subject.

Further provided in some embodiments of the present methods is a step of generating an image based on observed labeled deposits. Exemplary methods can also include a step of providing a reference profile of deposits, wherein the reference profile is the profile expected to be seen for a subject that is at a particular stage of age-related macular degeneration, including one that does not suffer from age-related macular degeneration. Some embodied methods also further comprise obtaining a subsequent profile of deposits in the subject. Further still, exemplary methods further comprise administering to the subject a treatment for age-related macular degeneration when the profile of deposits in the subject is associated with age-related macular degeneration.

Additionally, the presently-disclosed subject matter can include methods for labeling or detecting deposits. Embodied methods include contacting a tissue sample with a HAP label or a HAP label compound that is described herein, and detecting a signal from the HAP label or HAP label compound. In some implementations the presence of the signal from the HAP label or HAP label compound indicates the presence of deposits, such as drusen, sub-retinal deposits, basal laminar or linear deposits, or combinations thereof. The sample can be an eye tissue sample, brain tissue sample, or the like. Furthermore, the contacting step includes administering eye drops comprising the HAP label or the HAP label compound to an eye of a subject or injecting a solution comprising the HAP label or the HAP label compound into vitreous humor within the eye of the subject. Also, the step of contacting can include contacting a retina of a subject with the HAP label or the HAP label compound.

The presently-disclosed subject matter also includes kits comprising the present labels. Some kits can comprise a HAP label or a HAP label compound as described herein, and a pharmaceutically acceptable carrier, the HAP label or the HAP label compound and the pharmaceutically acceptable carrier being packaged together in a container. The pharmaceutically acceptable carrier can be an aqueous eye drop solution or a solution for injection into vitreous humor of the eye. For the eye drop solution, the container is configured to administer a solution in a dropwise manner. The container can also be a syringe or other container.

Further still, the presently-disclosed subject matter includes pharmaceutical compositions comprising comprising any of the compounds described or suggested herein and one or more pharmaceutically acceptable excipients. In some embodiments the pharmaceutical composition is suitable for delivery to the eye.

Further features and advantages of the present presently-disclosed subject matter will become evident to those of ordinary skill in the art after a study of the present application.

DESCRIPTION OF EXEMPLARY EMBODIMENTS

Figure 1:
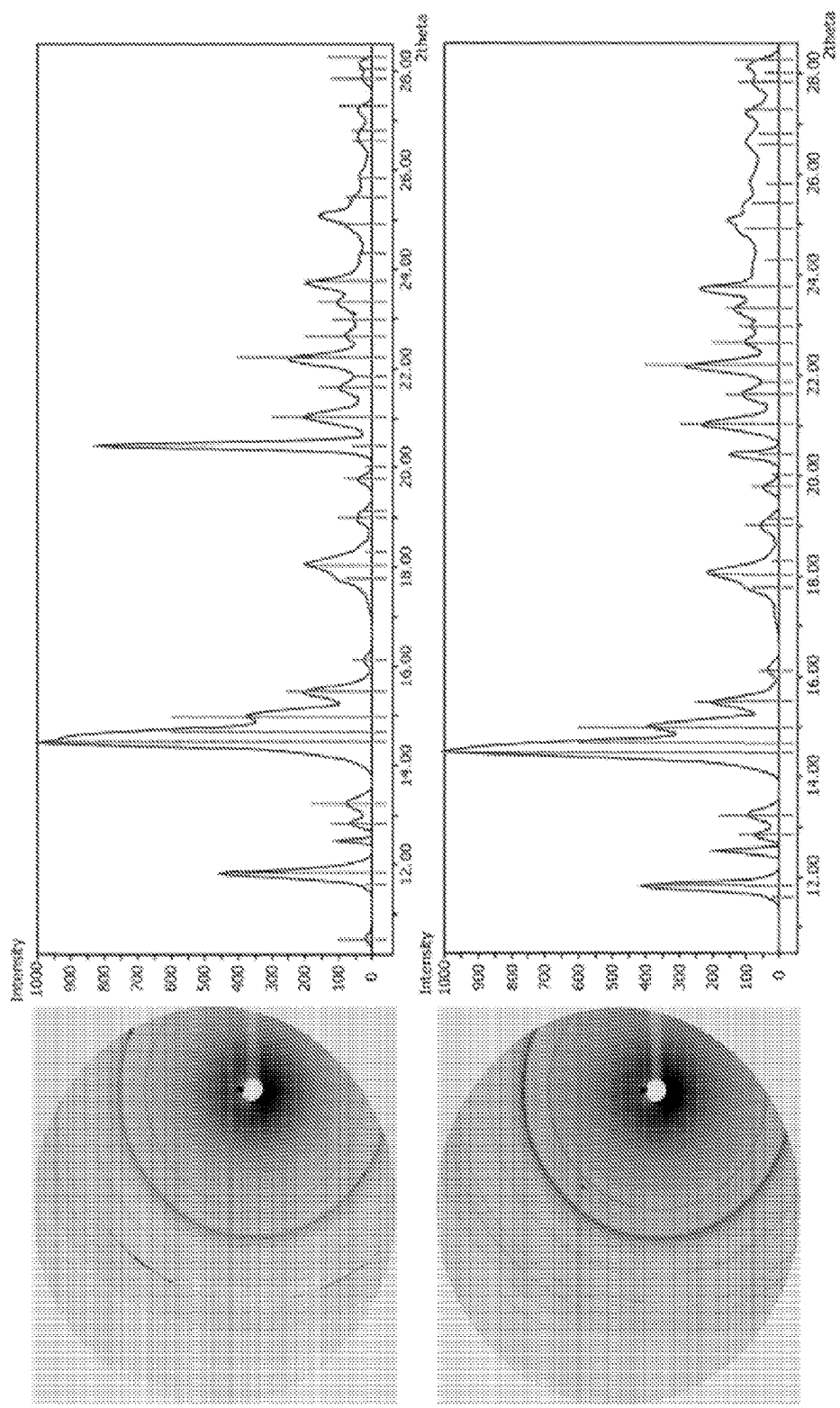
FIG. 1 includes X-ray diffraction patterns (left panels) and radial intensity profiles (right panels) of hydroxyapatite in drusen. Red lines indicate the position of peaks for pure HAP powder diffraction.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter meets some or all of the above-identified needs, as will become evident to those of ordinary skill in the art after a study of information provided in this document. To avoid excessive repetition, this Description does not list or suggest all possible combinations of such features.

The present inventors have identified that hydroxyapatite (HAP), a highly insoluble basic form of calcium phosphate ($3Ca_3(PO_4)_2 \cdot Ca(OH)_2$) that is the principal mineral in bone and teeth and is a significant constituent of sub-retinal deposits (e.g., drusen), which can be observed in age-related macular degeneration (AMD). HAP is marked by the additional hydroxide ions in its structure, is generally formed under more basic conditions than the mono- and dibasic calcium phosphates seen in tissue calcification, and is much less soluble ($K_{sp} \approx 10^{-58}$) and more stable than the other calcium phosphate forms. Furthermore, while amorphous calcium phosphate associated with the elastin layer of the Bruch's membrane and calcium ions can be present in within the Bruch's membrane and the sub-RPE, the present inventors identified that the observed HAP is not primarily in the elastic layer of the BM, but is instead associated with sub-retinal deposits, such as drusen.

The present inventors identified compounds that bind HAP, fluoresce, and bind to sub-retinal deposits. The compounds permitting earlier and accurate detection of such deposits and earlier detection of macular degeneration such as AMD, and identification of individuals with an increased likelihood of developing macular degeneration such as AMD. The labels therefore can permit one to monitor the progression or regression of sub-retinal deposits by, for example, fluorescence ophthalmoscopy. The present inventors also identified that it is possible to detect HAP-containing deposits on the inner surface of the Bruch's membrane, above the inner collagenous layer, even at a stage when no deposits can be seen clinically or microscopically in post-mortem tissues.

Accordingly, the presently-disclosed subject matter provides a hydroxyapatite (HAP) label for use in the identification or labeling of drusen or other similar deposits, especially sub-retinal deposits such as basal laminar or linear deposits.

A hydroxyapatite (HAP) label is any agent that binds substantially specifically to HAP and which allows its presence to be identified, for example by means of a signal. That means, it includes one or more moieties which bind to HAP in preference to other compositions and labels it. In some embodiments the HAP label comprises a signal generating moiety that can produce a detectable signal or the like. In some embodiments the HAP label comprises one moiety that is configured to be a HAP-binding moiety and also is configured to be a signal generating moiety (e.g., PAM-78). Thus, in some embodiments the label can comprise one moiety that can serve as both a HAP-binding moiety and a signal generating moiety. In further embodiments the HAP label comprises a first moiety that is a HAP binding moiety and a second moiety that is a signal generating moiety. The HAP binding moiety includes compounds that bind specifically to HAP, including, but not limited to, tetracycline derivatives, xylenol orange, alizarin (e.g., alizarin red), calcein, phosphonates (e.g., bis-phosphonates), and pamidronate. Peptides that bind HAP are also known from the art. It is possible to identify whether a compound binds to HAP using standard binding assays.

The HAP label allows the presence of HAP to be identified by any appropriate means. Often, the label can produce a signal which may be detected from outside the tissue in which the deposit is found. For example, the signal generating moiety can be a visualisable or optical label, detectable by optical methods, including fluorescence, fluorescence lifetime, fluorescence lifetime imaging, fluorescence polarization or anisotropy, chemiluminescence, phosphorescence, bioluminescence, Raman scattering, absorption, polarimetry, and second harmonic generation. Alternatively or in addition to visualisable or optical labels, the label can comprise a signal generating moiety that is a non-optical label. Exemplary non-optical labels include, but are not limited to, those that comprise $^{99m}Tc$ for SPECT or paramagnetic lanthanide complexes for MRI. Alternatively it may be a radioactive label. It is preferred that the signal generating moiety is a fluorescent label.

Fluorescent labels can be selected based on their emission and/or excitation spectrums. In some embodiments the fluorescent label is selected based on potential interfering fluorescence, absorption, and/or scattering. In some embodiments the labels comprise fluorescent labels that include an emission and/or excitation spectrum in the visible or infrared range of the optical spectrum, especially the infrared or near infrared range. In particular, it is preferred that the label has an emission spectrum having a wavelength of at least 450 nm and/or of less than 1800 nm. In this regard, the emission spectrum can have a wavelength of about 450 nm, 550 nm, 600 nm, 650 nm, 700 nm, 750 nm, 800 nm, 850 nm, 900 nm, 950 nm, 1000 nm, 1050 nm, 1100 nm, 1150 nm, 1200 nm, 1250 nm, 1300 nm, 1350 nm, 1400 nm, 1450 nm, 1500 nm, 1550 nm, 1600 nm, 1700 nm, 1750 nm, 1800 nm, or any values there between. In one embodiment the signal generating moiety is Dyomics dye DY-776. In others it is Dyomics Dye 781, Licor IRDye 680 or IRDye 800, or PAM-78 as described in U.S. Pat. Nos. 6,869,593 and 7,374,746. Having an emission spectrum in this spectral regime allows the label to be easily identified, especially when it is used to label sub-retinal deposits, as the infrared emission passes through the retinal pigmented epithelial layer and there is minimal interfering fluorescence. The emission and/or excitation spectrum can also be in the ultraviolet, blue, or another range in some embodiments.

The HAP label may be a compound which binds HAP and is also itself visualisable, or otherwise identifiable, such as the tetracycline derivatives and alizarin red, which bind HAP and are fluorescent. Alternatively, the HAP label may comprise a HAP binding moiety, itself visualisable or otherwise, conjugated to a signal generating moiety, such as a phosphonate, such as bis-phosphonate, pamidronate, or bis-iminodiacetate. That is to say, in the HAP label, the HAP binding function and labelling (signal generating) function may be provided by the same or different moieties. Also provided by the presently-disclosed subject matter is a HAP label, comprising a HAP binding moiety, such as a calcium chelating agent or other moiety, conjugated to DY-776.

It is particularly preferred that the label exhibits a change in the signal upon binding to the HAP, because the change in signal makes the presence of HAP easier to detect, and provides visual contrast. For example, Alizarin Red S exhibits a substantial increase in fluorescence quantum yield upon binding HAP, making the identification of HAP in images easier. Similarly, tetracycline exhibits a substantial increase in fluorescence lifetime upon binding HAP, permitting HAP to be identified by fluorescence lifetime imaging methods known to the art.

The presently-disclosed subject matter can also include methods for screening compounds for their ability to label and detect the presence of HAP. The method can comprise contacting a candidate compound with HAP to determine whether the compound binds and/or emits a detection signal upon binding HAP. The method can also comprise contacting a candidate compound with drusen or a similar deposit to determine whether the compound binds and/or emits a detection signal upon binding.

The present HAP label is particularly for use in diagnosing or predicting the likelihood of having or developing a neurodegenerative disease, or assessing the status of a neurodegenerative disease in a subject, the neurodegenerative disease being associated with the presence of sub-retinal deposits like drusen or other similar deposit. In particular, it may be a neurodegenerative disease associated with the presence of drusen or other deposits in the retina, such as age-related macular degeneration, retinitis pigmentosa, Parkinson's disease, Alzheimer's disease, macular telangiectasia, Stargardt disease, and long term retinal detachment. Alternatively it may be Huntington's disease, Transmissible spongiform encephalopathy, Diabetes mellitus type 2, Medullary carcinoma of the thyroid, Cardiac arrhythmias, Isolated atrial amyloidosis, Atherosclerosis, Rheumatoid arthritis, Aortic medial amyloid, Prolactinomas, Familial amyloid polyneuropathy, Hereditary non-neuropathic systemic amyloidosis, Dialysis related amyloidosis, Finnish amyloidosis, Lattice corneal dystrophy, Cerebral amyloid angiopathy, Cerebral amyloid angiopathy (Icelandic type), systemic AL amyloidosis, and Sporadic Inclusion Body Myositis. It is particularly one of age-related macular degeneration, retinitis pigmentosa, Parkinson's disease, Alzheimer's disease, macular telangiectasia, Stargardt disease, long term retinal detachment, especially age-related macular degeneration or Alzheimer's disease.

In this regard, the terms "diagnosing" and "diagnosis" as used herein refer to methods by which the skilled artisan can estimate and even determine whether or not a subject is suffering from a given disease or condition. Along with diagnosis, clinical "prognosis" or "prognosticating" is also an area of great concern and interest. It is important to know the relative risk associated with particular conditions in order to plan the most effective therapy. If an accurate prognosis can be made, appropriate therapy, and in some instances less severe therapy or more effective therapy, for the patient can be chosen. In some embodiments of the presently disclosed subject matter, a method includes identifying a subject as having a neurodegenerative disease (e.g., age-related macular degeneration) if the presence of HAP-containing deposits are identified in a tissue (e.g., eye or brain) sample obtained from a subject.

The deposits may be drusen or other sub-retinal deposits in the eye, or similar deposits found elsewhere, such as in the brain. Sub-retinal deposits that include basal laminal, basal linear deposits, and sub-RPE deposits.

As indicated, the HAP label is particularly useful for labeling deposits in the eye. Accordingly, it may be formulated for delivery to the eye, for example for topical delivery, as an eye drop comprising an eye drop solution, or for intravitreal or other intraocular injection. Alternatively, it could be for detecting or labeling deposits in the brain, vascular tissues, or other tissues. Accordingly, it may also be formulated for systemic administration, for example as an intravenous injection or the like. Systemic administration may also be appropriate when the target tissue is in the eye. The HAP label may be combined with any appropriate pharmaceutical adjuvants, carriers, and/or excipients necessary or advantageous for the delivery method selected.

In this regard, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use. In some embodiments the formulations are contained in containers that can dispense the solution in a dropwise manner. Such containers are particularly beneficial for administering eye drop formulations comprising the present labels and compositions.

Liquid preparations can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid).

Preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner. For ocular administration the composition can take the form of an aqueous solution comprising the present label and/or the present label compounds and a pharmaceutically acceptable carrier. The carrier can be an aqueous solution optionally comprising other substances that can be used in eye drop solutions, such as polyethylene, ions, salts, and other pharmaceutically active agents.

Diagnosis or prediction of neurodegenerative disease in a subject may be achieved by, for example, administering the HAP label to a subject and then scanning the subject for the labeled deposits. In particular, the HAP label may be administered to the eye of the subject, for example in the form of an injection, or as an eye drop. The retina of the subject may then be scanned using a for example a fluorescent scanning ophthalmoscope to identify the presence of the deposits.

Diagnosing or predicting the likelihood of having or developing a neurodegenerative disease, or assessing the status of a neurodegenerative disease in a subject, preferably means obtaining information which enables a clinician to decide whether a subject has a neurodegenerative disease or is likely to develop a neurodegenerative disease, or to monitor the progression or regression of a neurodegenerative disease. The information obtained may allow the clinician to make a diagnosis directly, or may rely on the combination of the presently-disclosed subject matter with other clinical signs or symptoms. Such information includes any information tending to show the presence, the progression, or the regression of HAP in a subject, as these factors may be indicative of a neurodegenerative disease and aid in the diagnosis thereof.

Diagnosis or prediction or assessment of neurodegenerative disease status may be achieved by, for example, identifying the presence or absence of deposits in a subject, especially in the retina of a subject, or obtaining a profile of the deposits in a subject, such as size, number, location etc.

A profile refers to any qualitative and/or quantitative analysis of the deposits in a subject. In some embodiments a profile refers to any qualitative and/or quantitate analysis of the HAP in a subject. Thus, a profile may include an image, a table, a chart, or the like that describes and/or quantifies the levels of deposits and/or HAP in a subject. The results may be compared with a reference deposit profile, that is to say the profile expected to be seen in a subject with or without the neurodegenerative disease in question. The reference deposit profile can also refer to a previous profile obtained from the same subject.

The presently-disclosed subject matter also provides methods and systems for predicting a neurodegenerative disease status, especially the status of one or more of age-related macular degeneration, retinitis pigmentosa, Parkinson's disease, Alzheimer's disease, macular telangiectasia and Stargardt disease. In some embodiments, a method is provided, which comprises administering a HAP label to a subject; obtaining a profile of deposits in a subject by observing the subject for labeled deposits, especially in the retina of a subject, and using the profile to predict a neurodegenerative disease status. The subject may be observed by, for example, scanning the subject, especially the retina of the subject for labeled deposits. It may also include generating an image of the labeled deposits. In this regard, scanning refers to any method for measuring a detectable signal from label that has been administered to a subject. Thus, as used herein, the term scanning can be used interchangeably with obtain a profile of a deposit.

In some embodiments, a system is provided, including a composition for labeling deposits in a subject and a machine for obtaining a profile of deposits in the subject.

In some embodiments of the presently-disclosed subject matter, the method and/or system includes providing a reference profile of deposits, wherein the reference profile is the profile expected to be seen for a subject that is at a particular stage of a neurodegenerative disease, which can be inclusive of subjects that do not suffer from a neurodegenerative disease. In some embodiments, the method and/or system includes predicting a neurodegenerative disease status based on the deposit profiles and/or difference between the subject deposit profile and the reference deposit profile. In some embodiments, the method and/or system includes comparing the profile and the reference profile.

In some embodiments of the presently-disclosed subject matter, the method and/or system includes obtaining a subsequent profile of deposits in the subject. In some embodiments, the method and/or system includes predicting a neurodegenerative disease status based on the deposit profiles and/or change (e.g., progression or regression) in the deposit profiles. In some embodiments, the method and/or system includes comparing the profile and the subsequent profile. In some embodiments, the method and/or system includes identifying changes, if any, between obtained profiles of deposits. In some embodiments, the method and/or system includes predicting a neurodegenerative disease status based on the identified changes, or lack thereof. In some embodiments, the neurodegenerative disease status is no substantial change, a progression of neurodegenerative disease, or a regression of neurodegenerative disease. In some embodiments, the method and/or system includes assessing a treatment program based on the identified changes, or lack thereof. In some embodiments, the subsequent profile of deposit is obtained following the initiation of a treatment program.

In this regard, the terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Thus, embodied methods can provide for methods of diagnosing a subject as having a neurodegenerative disease, and can further provide information for directing the therapies intended to cure, ameliorate, stabilize, or prevent such diseases. With respect to age-related macular degeneration, treatment can include administration of anti-angiogenic agents, including sorafenib, sunitinib, pazopanib, everolimus, VEGFR-1, NRP-1, angiostatin, endostatin, vasostatin, calreticulin, prolactin, esteopontin, maspin, canstatin, restin, and the like. Other treatments can include laser therapy, photodynamic laser therapy, vitamin, such as vitamins C, E, beta-carotene, zinc, and copper, submacular surgery, and retinal translocation.

Also, as used herein, the term "subject" includes both human and animal subjects. Thus, veterinary therapeutic uses are provided in accordance with the presently disclosed subject matter. As such, the presently disclosed subject matter provides for the treatment of mammals such as humans, as well as those animals of importance (e.g., due to being endangered, of economic importance, of social importance, etc.), including, but not limited to primates. Alternatively, the subject may be a mammal or bird used as an animal model, thus providing diagnostic uses, and methods of testing for compounds useful for detecting HAP-containing deposits and/or treating amyloidosis or neurodegenerative diseases. Such subjects include rodents, especially mice, rats and rabbits, larger mammals, such as dogs, pigs, cats and sheep, or even birds such as quail or turkey. When the subject is a rodent, it may be an APPS1 mouse or other rodent model of neurodegenerative disease.

Having identified HAP as being a significant and identifiable component of drusen and other similar retinal deposits, the inventors realised that the HAP could be used to target active agents to the deposits and to the relevant layers of the retina. Targeting agents in this way would not only enable them to be delivered to the correct site, but also, if desired, to delay the removal of said agents from the target site. One of the problems with delivering drugs to the eye is that they are washed out of the vitreous, and have to be administered repeatedly. By targeting the active agents to the target site, it should be possible to reduce the rate at which they are removed from the eye and thereby reduce the frequency of administration needed. Accordingly, there is provided a HAP binding moiety conjugated to an active agent. The agent may be therapeutically or pharmaceutically active, such as an anti-inflammatory, anti-oxidative agent or an anti-angiogenic agent. It may be particularly advantageous to target an anti-angiogenic agent to the deposits, for targeted treatment of AMD. In particular, the active agent may be a biologic agent, such as a peptide or an antibody or the like, or a small molecule pharmaceutical agent. It is particularly preferred that the active agent is an anti-angiogenic antibody or fragment thereof, such as ranibizumab or bevacizumab. Alternatively, it may be useful to use the label comprising the HAP binding moiety to deliver groups that will target the deposit and either break it down or, for example, coat it to prevent it triggering inflammatory or other reactions, such as a complement reaction. For example, the HAP binding moiety may deliver polyethylene glycol to allow the deposit to be coated.

Also provided is a method of labelling drusen or similar deposits in a tissue sample, comprising administering a HAP label to the sample and observing the sample for labelled deposits. The sample may be any tissue, such as tissue obtained from a subject, in which case the method may be for diagnosing a neurodegenerative disease in that subject. Alternatively, it may be a cultured tissue sample. It may be any type of tissue, especially eye tissue, brain or other neurological tissue, or vascular tissue.

The presently-disclosed subject matter is further illustrated by the following specific but non-limiting examples. Some examples are prophetic. Some of the following examples may include compilations of data that are representative of data gathered at various times during the course of development and experimentation related to the presently-disclosed subject matter.

EXAMPLES

Example 1

The preparation of the tissues was conducted with full Local Research Ethics Committee approval and appropriate consent were obtained in each case. The protocol of the study adhered to the tenets of the Declaration for Helsinki regarding research involving human tissue.

Microprobe synchrotron X-ray fluorescence (mSXRF) was used to map the spatial distribution of trace elements in sub-RPE deposits using beam lines X26 and X27A (National Synchrotron Light Source; Brookhaven National Laboratory, Upton, N.Y.). This is a non-destructive technique which measures the total amount of metals present in a sample. In mSXRF incident X-ray radiation is absorbed by and re-emitted from the sample in an energy-dispersive spectrum, where the frequency of the fluorescent radiation depends on the binding energies of the metal. This method can be used to measure the metal concentrations at one place, or to determine the distribution across an area. The incident X-ray radiation is absorbed throughout the thickness of the sample. By measuring the number of photons emitted at specific frequencies the relative concentrations of a metal can be determined in different samples with detection limits of transition metals ranging from 0.1 to 5 ppm. Bright-field and ZP 1 stained images were also made for orientation and determination of the presence and distribution of trace elements. The incident X-ray beam was tuned to 10 keV using a Si(111) channel-cut monochromator. This monochromatic beam is collimated to 400 mm in diameter using a set of tantalum slits and then focused to 5e10 mm in diameter using Rh-coated silicon micro-focusing mirrors in Kirkpatricke Baez type geometry. Energy dispersive X-ray fluorescence data were collected using a Canberra 9-element Ge Array detector (Canberra Industries, Inc., Meriden, Conn.). A spatial resolution of 10 mm was used with a 7 s integration time for scans of large retinal areas, and 10 s/pixel for rescans of specific sub-RPE deposits. For quantitative evaluations, brain-matrix standards were made from cryostat-prepared sections (20 mm) of homogenized fresh sheep isocortex spiked with different concentrations of trace metals. Emission values from the air-dried standards were used for calculation of trace metal concentration in the scanned tissues in ppm.

Alizarin Red S (9,10-dihydro-3,4-dihydroxy-9,10-dioxo-2-anthracenesulfonic acid; CAS no. 130-22-3) and Tetracycline hydrochloride (CAS no. 60-54-8) were both from Sigma-Aldrich (St. Louis, Mo.); IRDye 680RD BoneTag (cat. No. 926-09374) was from LiCor (Omaha, Nebr.), and all were used without further purification. Hydroxyapatite Bio-Gel HTP resin (Bio-Rad catalog 130-0420) (Bio-Red Laboratories, Inc., Hercules, Calif.) was used as a model for hydroxyapatite in deposits for purposes of collecting emission spectra; stained resin particles were suspended in propylene glycol for fluorescence spectroscopy. Calcium phosphate tribasic (34-40% Ca basis, cat no. C5267), Calcium hydrogen phosphate dihydrate (dibasic, 98%, cat. No. 307653) and calcium phosphate monobasic monohydrate (>85%, cat no. 21053) were all products of Sigma Aldrich and used without further purification. Fluorescence spectra were obtained on a Spectronics AB-2 spectrophotofluorometer with a high pressure xenon lamp.

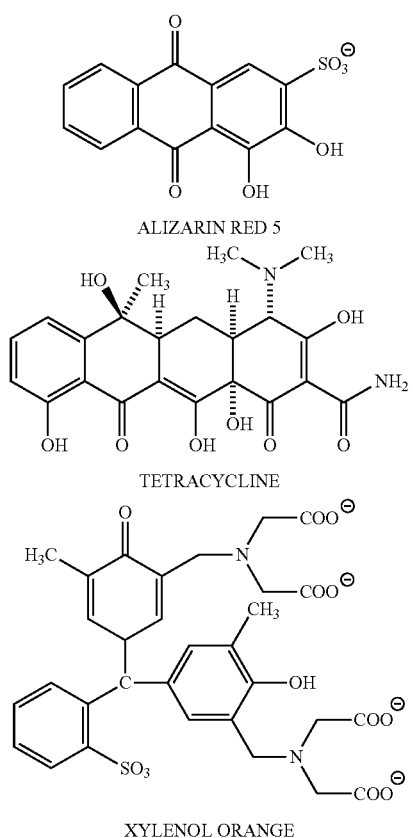

Retinal specimens prepared as above were immersed in solutions of Aizarin Red or tetracycline (1 mg/ml in water), or 2 ng/50 ul LiCor 680 dye in water for 15 minutes, flat-mounted on cover slips, and imaged on a Nikon Eclipse E200 epifluorescence optical microscope (Nikon Corporation, Tokyo, Japan) with a high pressure Hg lamp excitation source, and using Nikon 4x/0.2 NA PlanApo and 20x/0.75 NA S Fluor objectives and a Cooke Sensicam QE CCD camera. Specimens were imaged through Omega XF15 (Tetracycline HCL, typically used for Quinacrine Mustard) and XF 22 (autofluorescence, for FITC) filter cubes; for imaging Alizarin fluorescence an Omega D-540-25X excitation filter, Omega 570DCXRU dichroic mirror and Nikon BA-435 emission filter were used. For confocal microscopy they were imaged using a Zeiss LSM 700 (Carl Zeiss, Oberkochen, Germany) upright laser scanning confocal microscope and Zeiss 64x/1.4 NA oil immersion objective: tetracycline fluorescence was excited with 405 or 488 nm lasers, Alizarin Red was excited with the 555 nm laser, LiCor 680RD Bone Tag was excited with the 650 nm laser, and tissue autofluorescence was excited with the 488 nm laser. Images were synthesized and displayed with ZEN software.

The x-ray diffraction pattern obtained for a large drusen was similar to the pattern from a hydroxyapatite powder standard derived from bone (FIG. 1). Other drusen exhibited patterns with similar spacings but sharper peaks and defined arcs, indicating greater order and crystalline character. Thus, the observations suggested the presence of HAP in the retina.

Alizarin Red S and Tetracycline HCl were first tested on an HAP chromatographic medium as a model for drusen; the particles were stained as described, rinsed in distilled water, and suspended in propylene glycol. Both stains produced bright fluorescence emission when bound to the HAP that did not rinse off despite repeated washes with buffer. The resulting fluorescence emission spectra were consistent with other observations of bone staining by Alizarin Red S and teeth staining by tetracycline (K. C Hoerman, *J. Dent Res.* 54, B131 (1975) "Spectral characteristics of tetracycline-induced luminescence in rat teeth and bones"). Alizarin Red S had a pH-dependent absorption spectrum; the uncorrected excitation spectrum of HAP-bound Alizarin Red S exhibited peaks at 556 and 596 nm (results not shown), similar to the absorption spectrum of the dye in 0.1N NaOH (Green, F. J., *The Sigma-Aldrich Handbook of Stains, Dyes, and Indicators,* Aldrich Chemical Co., Milwaukee, Wis. (1990), pp. 80-81). Both stains also stained samples of tribasic calcium phosphate, and dibasic calcium phosphate less well than HAP; monobasic calcium phosphate was slightly soluble and no staining was evident. The tribasic form is also listed on the label as "hydroxyapatite" and specified to contain 34-40% of calcium by weight; thus it appears to contain substantial proportions of both tribasic calcium phosphate and hydroxyapatite. The dibasic form of calcium phosphate is listed as 98% pure. It did not appear that either stain was adhered to insoluble zinc phosphate. IRDye 680RD BoneTag was also tested on HAP and drusen. This probe is a long wavelength excitable fluorophore coupled to tetracycline designed as an in vivo bone stain (J. L. Kovar et al., 2011 Anal. Biochem. 416(2):167-173). It stained HAP very well; its long wavelength of absorption and emission largely avoided autofluorescence from the retinal tissues.

Sub-RPE deposits were first visualized by their characteristic autofluorescence in blue light. Samples were then viewed at lower power using reflected light under bright field to identify the opaque sub-RPE deposits on the surface of BM. There were numerous small (~10 µm) and larger (>100 µm) drusen detected in all samples. In the macula there was a continuous layer of deposition with varying thickness that covered large areas of BM. Here sub-RPE deposits appeared to have less defined shapes reminiscent of soft drusen.

In testing the three stains on cadaver posterior retinas, tetracycline staining gave about an eight-fold increase in apparent intensity over the fluorescent background of the sub-RPE alone and Alizarin Red S gave about a fifteen-fold increase in intensity. Tetracycline exhibits about a twentyfold increase in intensity and apparent lifetime (results not shown) upon binding HAP, so the more modest apparent increase is a reflection of the substantial autofluorescence background of the posterior retina. Exciting HAP-bound tetracycline near the peak of its absorbance at 410 nm instead of 488 nm improved its signal level significantly, but the level of background fluorescence also increased substantially, so the net improvement is less marked. The background fluorescence of the tissue at the wavelength of Alizarin Red S excitation (550-600 nm) and emission (650 nm) is much less, providing nearly two-fold better contrast than tetracycline. However, the pigment granules do exhibit significant fluorescence at these wavelengths.

The LiCor stain provided much the best results. In a confocal Z-stack (FIG. 2a) the dye stains (excitation 650 nm, Emission 680+nm) small spheres in the sub-RPE deposits and drusen, with practically no other background except very slight staining in the choroid. The autofluorescence image in the same figure clearly delineated the boundaries of the Bruch's membrane and choroid, but the lack of diffuse pink staining in the figures makes clear the low background at the LiCor stain's wavelengths; in addition, pigment granules from the RPE exhibited very low emission at these wavelengths. No staining by Alizarin Red S or the LiCor dye of the elastin layer of the Bruch's membrane was observed, which can become calcified in some circumstances.

The stained spheres were sometimes stained all the way through, whereas in other cases they were conspicuously hollow. This is similar to the layers of particular proteins observed in drusen by immunofluorescent staining, including vitronectin, complement factors B, 3, and H. This suggests a layering of protein on a nucleating particle; perhaps in some cases the nucleating particle may be hydroxyapatite.

The unexpected finding that hydroxyapatite (HAP), a basic form of calcium phosphate, was present in drusen led to the identification of fluorescent compounds binding HAP as drusen stains. Tetracycline and Alizarin Red S are used to fluorescently stain mineralized tissue including bone and teeth (H. Villman, "The in vivo staining of bone with Alizarin Red S," *J. Anatomy* 105 533-545 (1969); and H. C. W. Skinner and J. Nalbandian, "Tetracyclines and mineralized tissues: review and perspectives," *Yale J. Biol. Med.* 48, 377-397 (1975)). The LiCor 680 RD Bone Tag stain (and a longer wavelength variant LICor 800CW Bone Tag, as well as fluorescent-labeled phosphonate Pam-78, (U.S. Pat. No. 7,374,746 to Frangioni)) are in vivo fluorescent stains for monitoring bone growth in living experimental animals. The fact that the compounds specifically stained the sub-RPE deposits, taken together with the characteristic X-ray diffraction pattern, is evidence that HAP is a component of sub-RPE deposits. The bright and selective fluorescent staining by both compounds indicates that these or similar compounds can permit detection of drusen in vivo well prior to their detection by standard ophthalmoscopes using reflected light or autofluorescence. The use of both compounds for in vivo animal studies of bone formation and tetracycline's widespread therapeutic use in humans indicates that at least some of these compounds should be safe for use in humans.

Example 2

Age-related Macular Degeneration (AMD) is the most common cause of irreversible visual loss in the elderly in developed countries. The incidence of the disease is growing with the increase in life expectancy all over the world, and it is anticipated that by 2040 there will be 300 million persons affected by AMD. AMD may present with early disease at which time focal deposits (i.e., drusen) can be seen at the back of the eye and visual acuity is normal. Late AMD, which may involve choroidal neovascularization (CNV) or geographic atrophy (GA), causes loss of visual acuity. If diagnosed early, CNV is treatable with antibodies to vascular epithelial growth factor. A major feature of AMD in all its stages is thickening of Bruch's membrane (BM) due to deposition of proteins and lipids. The deposits may be focal (drusen) or diffuse (basal linear and laminar deposits). Bruch's membrane is interposed between the retina and its source of nutrition, the choroid, and it is thought that the deposits act as a barrier to metabolic exchange, thus contributing to visual loss. Sub-RPE deposits appear to be initiated over the pillars of the choroidal micro capillaries, increase in number and size with age, and are widely believed to impair metabolic exchange between the blood circulation and the retina. Substantial effort has been devoted to understanding the composition and origin of sub-RPE deposits, with a view to developing better diagnosis, prevention, and treatment. Despite the large body of genetic, biochemical, molecular and cell biology evidence for the involvement of proteins and lipids in AMD, there is no unifying explanation of how and why they are deposited at the RPE/choriocapillaris interface to form focal (drusen) or diffuse (basal linear or laminar) deposits. This Example therefore describes procedures conducted to characterize and identify the mechanism between the formation of deposits (drusen, basal linear, laminar, etc.), and how such mechanisms can be used for the diagnosis and prediction of AMD.

Because retinal pigment epithelial (RPE) cells contribute to drusen deposition, ARPE-19 cells (human RPE cell line) were selected for this Example. For stable isotope labelling with amino acids in cell culture (SILAC) experiments, cells were grown in SILAC DMEM:F12 medium (PAA Laboratories) supplemented with 10% dialyzed fetal bovine serum (PAA Laboratories), 1% (v/v) penicillin-streptomycin and $^{12}C_6$, $^{14}N_2$ lysine plus $^{12}C_6$, $^{14}N_4$ arginine (light medium) or $^{13}C_6$ lysine plus $^{13}C_6$,$^{15}N_4$ arginine (heavy medium). 0.5 mM proline was added to all SILAC media to prevent arginine-to-proline conversion. All amino acids were obtained from Silantes (Silantes GmbH, Munich, Germany). Subconfluent cultures were thoroughly washed with PBS and kept in serum-free medium for 24 hours. Label-swap replication was used for enhanced reliability in affinity ratios. Equal amounts of "heavy" supernatants were incubated either with BCMAG™ hydroxyapatite-coated magnetic silica beads (Bioclone, San Diego, Calif.) or with unmodified silica-beads (negative control). "Light" supernatants were processed in the same way. After incubating overnight on a rotator at 4° C., bound proteins were eluted in Laemmli buffer (50 mM Tris, pH 6.8, 1% SDS, 10% glycerol, 100 mM β-mercaptoethanol, and Bromophenol Blue) for 15 min at 37° C. with gentle agitation. The corresponding samples (eluates from light-labeled HAP and heavy-labeled control beads and vice versa) were mixed and prefractionated by standard SDS-PAGE followed by tryptic in-gel cleavage before being subjected to LC-MS/MS.

LC-MS/MS analysis was performed on an Ultimate3000 nano HPLC system (Dionex Corporation, Sunnyvale, Calif.) coupled to a LTQ OrbitrapXL mass spectrometer (Thermo Fisher Scientific, Waltham, Mass.) by a nano spray ion source. Tryptic peptide mixtures were automatically injected and loaded at a flow rate of 30 μl/min in 95% buffer C (0.5% trifluoroacetic acid in HPLC-grade water) and 5% buffer B (98% acetonitrile and 0.1% formic acid in HPLC-grade water) onto a nano trap column (100 μm i.d.×2 cm, packed with Acclaim PepMap100 C18, 5 μm, 100 Å; Dionex). After 5 minutes, peptides were eluted and separated on the analytical column (75 μm i.d.×15 cm, Acclaim PepMap100 C18, 3 μm, 100 Å; Dionex) by a linear gradient from 5% to 40% of buffer B in buffer A (2% acetonitrile and 0.1% formic acid in HPLC-grade water) at a flow rate of 300 nl/min over 90 minutes. Remaining peptides were eluted by a short gradient from 40% to 100% buffer B in 5 minutes. The eluted peptides were analyzed by the LTQ OrbitrapXL mass spectrometer. From the high-resolution mass spectrometry prescan with a mass range of 300-1,500, the 10 most intense peptide ions were selected for fragment analysis in the linear ion trap if they exceeded an intensity of at least 200 counts, and if they were at least doubly charged. The normalized collision energy for collision-induced dissociation was set to a value of 35, and the resulting fragments were detected with normal resolution in the linear ion trap. The lock mass option was activated, the background signal with a mass of 445.12002 was used as lock mass. Every ion selected for fragmentation was excluded for 30 seconds by dynamic exclusion. For SILAC experiments, all acquired spectra were processed and analyzed using MaxQuant software (version 1.3.0.5) and the human-specific IPI database version 3.78 (www.maxquant.org/) in combination with Mascot (version 2.2; Matrix Science, Boston, Mass.). Cysteine carbamidomethylation was selected as fixed modification; methionine oxidation and protein acetylation were allowed as variable modifications. The peptide and protein false discovery rates were set to 1%. Contaminants such as keratins were removed. Proteins identified and quantified by at least 2 peptides per experiment were considered for further analysis. Each experiment consisted of a forward and a reverse labeling approach (label swapping) to exclude label-specific effects. A P value of 0.001 was selected as threshold for significant enrichment or alteration.

Eight human eyes with sub-RPE deposits were obtained from the Moorfields Eye Hospital Eye Depository (London, United Kingdom). Donor ages were between 60 and 95 years. Samples were obtained within 24 hours of death. Full Local Research Ethics Committee approval and appropriate consent were obtained in each case. The protocol of the study adhered to the tenets of the Declaration for Helsinki regarding research involving human tissue. The neural retina and the retinal pigment epithelial cells were removed by gentle agitation in phosphate buffered saline (PBS) to expose the underlying sub-RPE deposits and BM. The tissue was washed in PBS to remove as much as possible of the cell debris originating from the RPE and the neural retina. The remaining BM/choroid complex was removed from the sclera and mounted on glass slides with the sub-RPE deposits facing upwards. None of the samples were fixed for these experiments.

Flat mounts were stained with 1 mg/ml Alizarin Red S (Sigma-Aldrich; Ex: 532 nm Em:620 nm), 20 μM Bone-Tag 680RD (Li-Cor; Ex: 620 nm Em:680 nm), 1 mg/ml tetracycline (Sigma-Aldrich; Ex: 405 nm Em: 570 nm), and 1 mg/ml Xylenol Orange (Sigma-Aldrich; Ex: 532 nm Em:570 nm) in aqueous buffer for 20 minutes at room temperature. Nile Red (Invitrogen, Carsbad, Calif.; Ex: 532 nm Em: 620 nm) was first dissolved in acetone and then diluted in aqueous buffer to 3.5 mg/ml and tissues were incubated for 20 minutes at room temperature.

Immunohistochemistry was also performed on unfixed flat mounted BM/choroid tissue, obtained as above. Flat mounts were blocked with goat serum, incubated with primary and secondary antibodies for 2 hours each at 30° C. The primary antibodies used were anti-complement factor H (Santa Cruz Biotechnology, Inc., Santa Cruz, Calif.; 1/100 dilution), anti-vitronectin (AbD Serotec, Raleigh, N.C., 1/200 dilution) and anti-amyloidβ (6E10, 1/100 dilution; Covance, Princeton, N.J.). Alexa-Fluor 488 Goat anti-rabbit and Alexa-Fluor 568 Goat anti rat secondary antibodies were from Invitrogen and used in 1/1000 dilution.

Samples were imaged using a Zeiss LSM700 confocal microscope through a 63×/1.2 NA Zeiss Neofluar objective. Flat mount sections of Bruch's membrane on glass slides were transported and stored at −20° C., then immediately prior to analysis were placed in a freeze dryer for four hours to ensure the samples were compatible with the vacuum conditions of the SIMS instruments.

Figure 9:
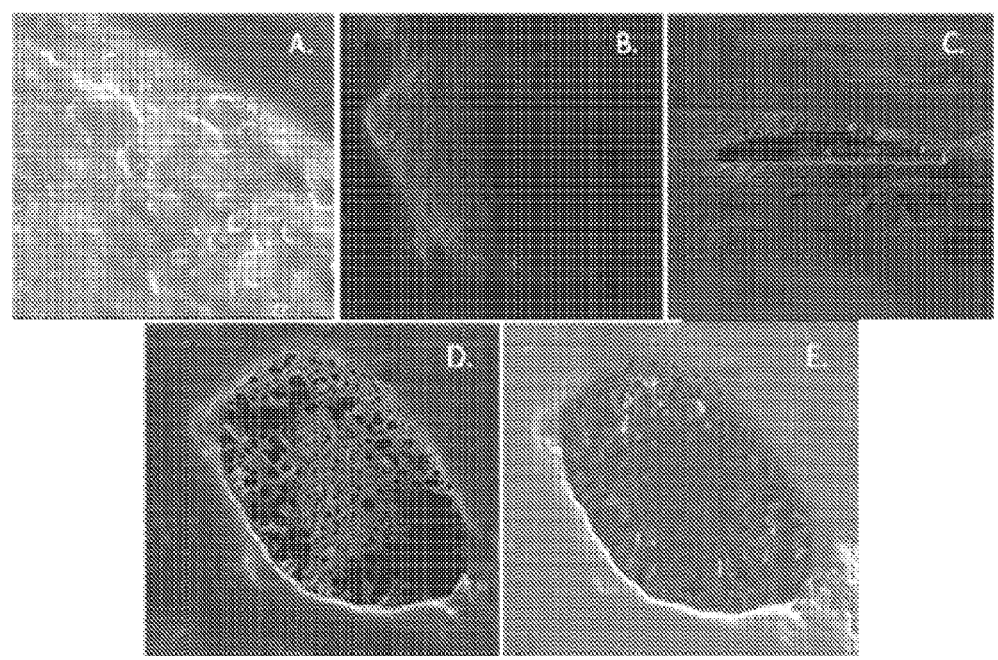
FIG. 9 includes images showing a focused ion beam (FIB) milling procedure where (A) drusen are identified with a large field secondary electron scan, (B) centered at higher magnification (B), rotated 90° so the ion beam is parallel to the sample surface allowing the upper portion of the drusen to be milled away, and rotated back to show the exposed surface to via secondary electron (D) and secondary ion (E) images.

In order to expose the internal structure of the drusen, a focused ion beam (FIB) milling approach was implemented using a FEI FIB200-SIMS. Following gold sputter coating to ensure a conducting surface, the glass slide was mounted on the rotating stage. The FIB system, using a highly focused gallium ion beam, allows secondary electron or secondary ion images to be obtained with ~10 nm resolution over a region of up to 500×500 micron. From an overhead position (FIGS. 9A and 9B), using a low current dose density to avoid damaging the sample, drusen could be located for the milling procedure. The sample is then rotated such that the ion beam is parallel to the surface of the sample. Using an increased ion beam current, the upper 1 μm is removed sequentially until the required region of the drusen is reached (FIG. 9C). By rotating back to the analysis position, secondary electron and secondary ion images can be obtained as a reference for the ToF-SIMS analysis (FIGS. 9D and 9E).

For mass spectrometry imaging at sub micron resolution over m/z 0-880, the slide was immediately transferred to a TOF.SIMS 5 (Iontof, Münster, Germany) secondary ion mass spectrometer. The system comprises of a bismuth primary ion beam, operating at 25 kV and tuned to use the $Bi_3^+$ cluster for greater secondary ion yield and a low energy electron flood gun for charge compensation. Ionic species sputtered from the surface under the bismuth bombardment are steered into a reflectron time-of-flight mass analyser.

Using the magnified video view of the sample and low ion dose density survey scans the milled drusen were located and centered into a 50×50 μm analysis area. Imaging of the region was performed in positive and negative ion detection modes, and ensuring the total ion dose was below the static limit where surface damage species become significant contributions to the total spectrum. For the survey scans the instrument was run in bunched mode (3 μm beam spot size on surface, mass resolution m/Δm 500) and in burst alignment mode (300 μm spot size, mass resolution m/Δm 500) for the higher spatial resolution imaging shown here. Peak masses from the higher mass resolution and mass accuracy survey scans were used to identify the peaks detected in the higher spatial resolution images.

Data analysis was carried out by first converting the data to a *.grd format using a recipe within the proprietary Iontof software. Subsequently the data was read into MATLAB (The Mathworks, Natwick, Mass.) using the GRDImport script freely available online All data analysis and visualization was performed using in house written MATLAB functions. Non-negative matrix factorization was performed on the data in order to reduce its dimensionality into five chemically distinct regions factors; the number of factors was chosen based on an Akaike information criterion analysis of a number of models. Peaks identified as strongly localized to the spherules and the general drusen inner compartment were identified from the factors and single ion images produced for the compilation of FIG. 3, for the overall protein signature a combination of characteristic immonium ions were summed, whilst the PC distribution was visualized by the PC headgroup peak at m/z 184.07 and cholesterol by its $[M+H-H_2O]^+$ ion at m/z 369.38.

Sunchrotron microfocused X-ray diffraction analyses (μXRD) of drusen were conducted at beamline X26A, National Synchrotron Light Source, Brookhaven National Laboratory. Tissue samples containing drusen were flat mounted on 4 μm thick ULTRALENE® film for analysis. Monochromatic X-rays were used tuned to an incident wavelength of 0.70926 Å using a channel-cut Si(111) monochromator crystal. The incident beam was focused to a spot size of 9(H)×5(V) μm on the sample using Rh-coated, silicon mirrors in a Kirkpatrick-Baez geometry. The X-ray diffraction from the sample was measured using a Rayonix SX165 CCD (Evanston, Ill.) area detector. Calibrations and corrections for detector distortions (camera—sample distance, camera tilt and rotation, and the beam center on the camera plane) were done using Fit2D™ software and corrected using NIST SRM 674a corundum standard and silver behenate. The 2D area detector data was integrated in to 2θ-intensity using Fit2D and HAP was then identified by comparison with reference powder-diffraction patterns (ICDD 2003) using the Match software (Crystal Impact, Bonn, Germany).

Figure 6:
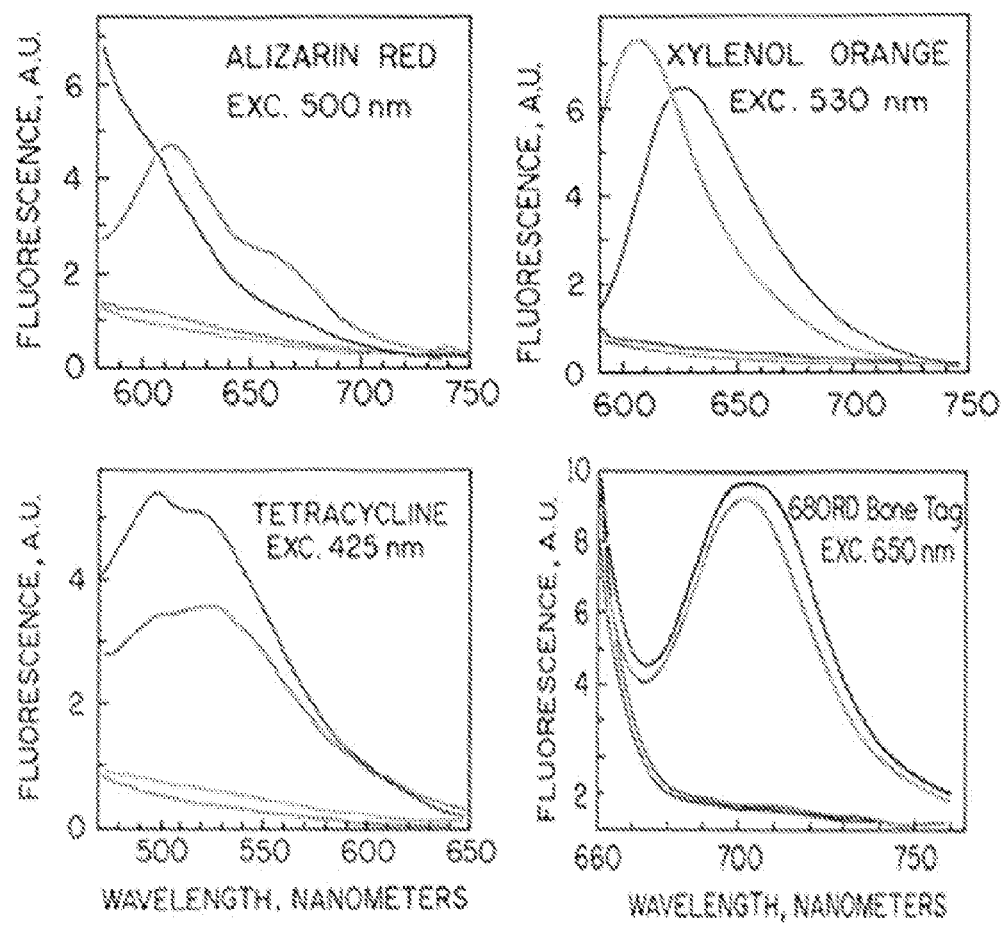
FIG. 6 includes fluorescence emission spectra of hydroxyapatite, dibasic calcium phosphate, and zinc phosphate suspended in propylene glycol following staining with Alizarin Red S (upper left panel, excitation at 500 nm), Xylenol Orange (upper right, 530 nm), Tetracycline HCl (lower left, 425 nm) and Bone Tag 680RD (lower right, 650 nm). Excitation and emission slits set at 4 nm, PMT voltage at 830 volts.
Figure 7:
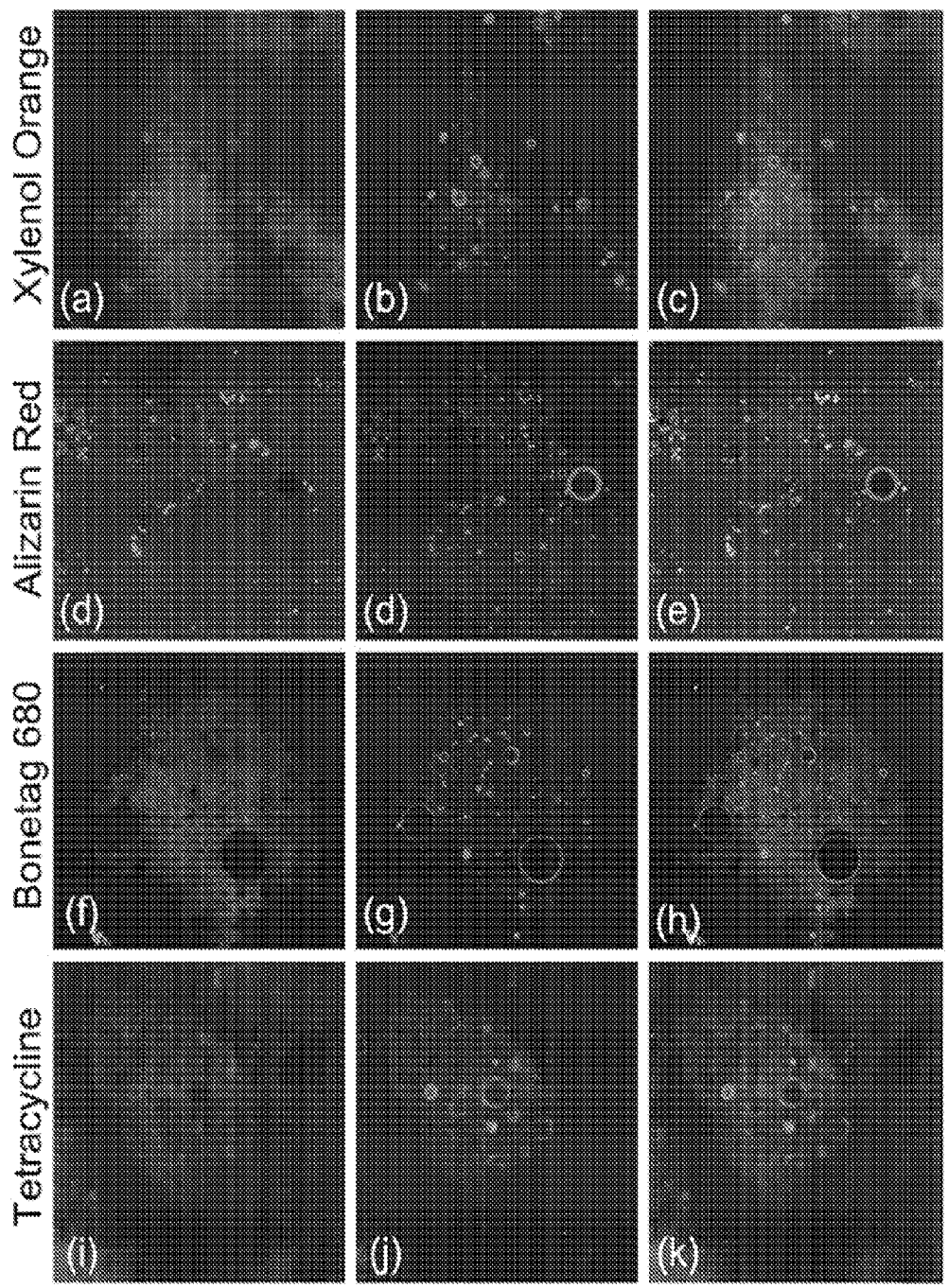
FIG. 7 includes autofluorescence images showing individual druse (a,d,f,i) (assigned colour in (i) changed to avoid overlapping emission spectra), showing labelling of HAP spherules with Xylenol orange (b), Alizarin Red S (e), BoneTag 680 RD (g), Tetracycline (j), and showing combined images thereof (c,e,h,k).

Alizarin Red S, Tetracycline HCl, and Xylenol Orange (FIG. 5) and LiCor Bone Tag 680RD (structure not available) were tested for their ability to fluorescently stain authentic hydroxyapatite, dibasic calcium phosphate, and, as a control for specificity, zinc phosphate. Briefly, the insoluble salts (100 mg in 1 ml 25 mM MOPS pH 7.5 buffer) were stained with 100 ul of 1 mg/ml dye (0.02 nmol/uL of the Bone Tag 680 RD dye) in buffer for 20 minutes at room temperature, followed by two rinses with buffer. Approximately 100 ul of the precipitate (a slurry) was suspended in propylene glycol. Fluorescence emission spectra shown in FIG. 6 were obtained at the excitation wavelengths described in the legend. Quantitation is no better than approximate since the level of Rayleigh scattering in these cloudy suspensions was large and variable. It can be generally seen in all cases that the only significant fluorescence from stained specimens is observed with hydroxyapatite. The fluorescence of the stained dibasic calcium phosphate and zinc phosphate were at least 3-fold to 10-fold lower under these conditions. Dibasic calcium phosphate and zinc phosphate did not stain significantly with any of the dyes, even though at physiological pH the dibasic form of calcium phosphate is most likely to be present. It thus appears that the dyes are specific for HAP under the experimental conditions. Therefore these 4 dyes were tested for their ability to stain HAP spherules in sub-RPE deposits in flat mounts of cadaver tissues (FIG. 7). Sub-RPE deposits can be readily identified based on their characteristic faint autofluorescence at excitation: 488 nm and emission: 525 nm). All dyes effectively stained spherules.

Microfocused synchrotron X-ray diffraction (μXRD) patterns from isolated human cadaver drusen were collected. The μXRD showed the presence of hydroxyapatite (HAP) in these drusen (Figure of merit=0.976, FIG. 1), suggesting it is present in sub-RPE deposits. Ectopic calcification of soft tissues has been associated with the general aging process, and significant calcification of the collagenous layer of BM is typically present in AMD. However, HAP is distinct from amorphous (largely dibasic) calcium phosphate found in ectopic calcification. Compared with dibasic calcium phosphate ($CaHPO_4$), HAP is much less soluble ($K_{sp}=10^{-7}$ vs $10^{-56}$), more stable, mechanically harder, and only solubilized by acid treatment, such as by osteoclasts in bone remodeling. HAP has not been described in the outer retina before, and it is possible that this is associated with the pathology of aging and especially of AMD.

Figure 2:
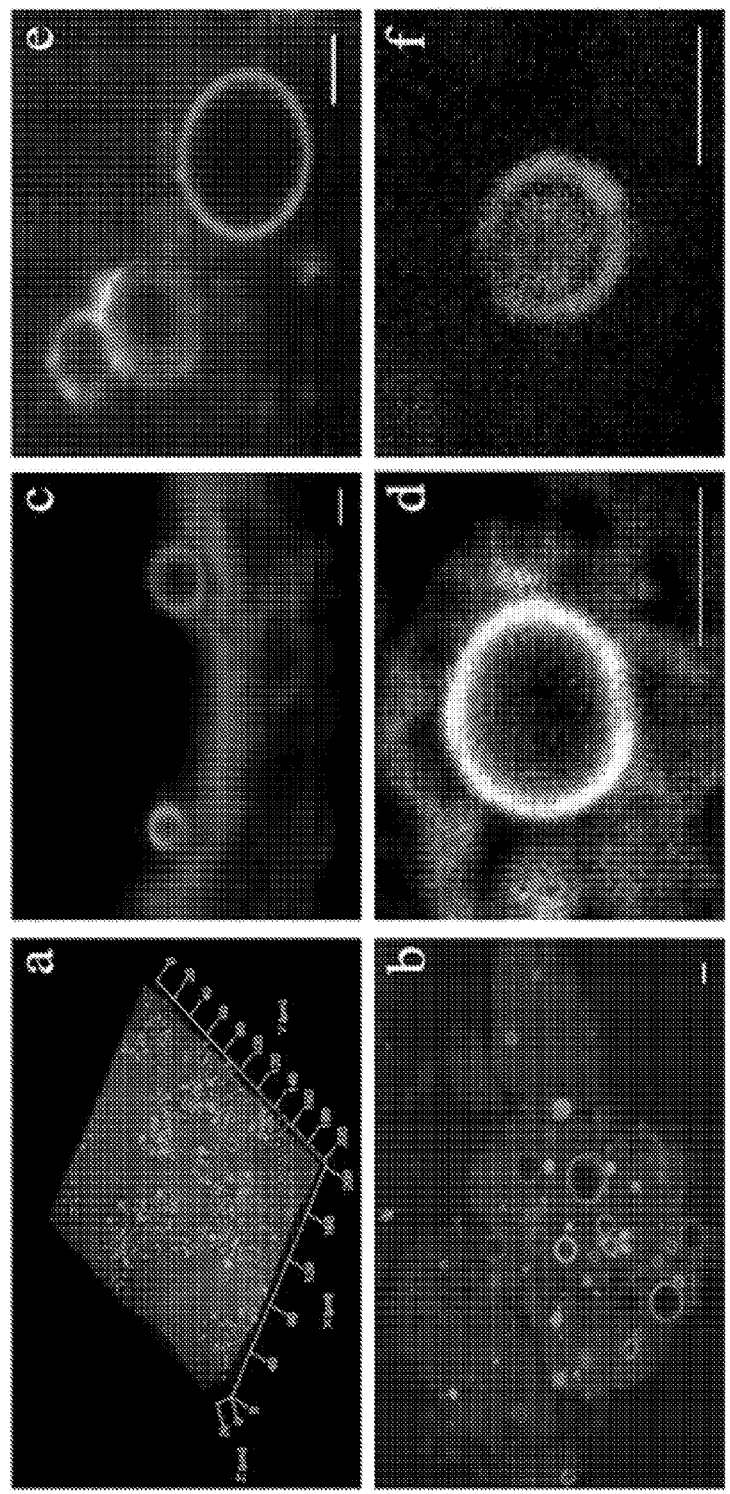
FIG. 2 includes confocal fluorescent micrographs showing hydroxyapatite (HAP) spherules in sub-RPE deposits viewed obliquely in a Z-stack (a), normal to the Bruch's membrane (b), and in the absence of sub-RPE deposits above the Bruch's membrane (c), and also shows HAP spherules coated with complement factor H (d), vitronectin (e), or Amyloid beta (f) following immunofluorescent staining Scale bars represent 2 micrometers in panel.
Figure 5:
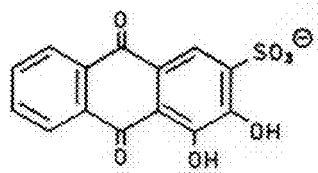
FIG. 5 includes chemical structures showing Alizarin Red S (top), Tetracycline (middle), and Xylenol Orange (bottom).
Figure 5:
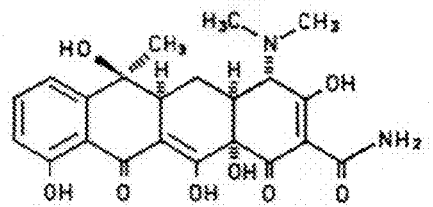
Figure 5:
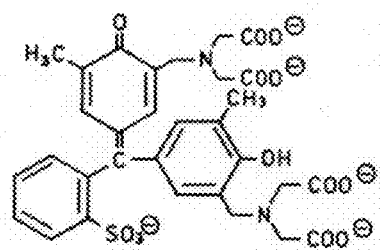

To better define the spatial distribution of HAP in drusen, four compounds known to fluorescently stain bones and teeth based on their HAP content were used to label sub-RPE deposits in human cadaveric eyes. These were tetracycline, its analog Bone-Tag 680 RD, Alizarin Red S, and Xylenol Orange. They all displayed very similar staining patterns in retinal tissue (FIG. 7) despite their differing HAP-binding moieties (FIG. 5). It is thus unlikely that they are binding with concomitant fluorescence enhancement to a single protein or lipid constituent of the deposits. These stains are specific for HAP in comparison to dibasic calcium phosphate or zinc phosphate (FIG. 6). Fresh, flat mounts of human cadaveric BM/choroid complex were stained following the removal of the neurosensory retina and the RPE with these dyes (FIGS. 2 and 7). Bone Tag 680 RD fluorescence is mainly present in small (0.5-20 um, average ~3 um) spherules within drusen, and distinct from the typical autofluorescence of the choriocapillaris, BM, and drusen themselves. The spherules exhibited a hollow appearance, in that the dyes did not stain the spherules all the way into their centers (FIG. 2b). The lack of staining of the core of the spherules was not the consequence of lack of penetration of dyes, as similar shells appear on sectioned specimens with HAP on the cut face (data not shown).

The shells shown in FIG. 2 are similar to images previously obtained by immunohistochemical staining of sub-RPE deposits for proteins such as amyloid beta, complement factor H (CFH), serum amyloid, and vitronectin. Since hydroxyapatite is known to bind proteins and is still widely used as a chromatographic stationary phase, this suggests that the HAP spherules generated through pathological process(es) may nucleate and promote growth of the protein-rich sub-RPE deposits by binding particular proteins present in the sub-RPE space. Immunostaining for other drusen-associated proteins does not show a spherular staining pattern, therefore it appears that there is a selectivity of protein binding to HAP. Co-labelling for HAP and selected proteins reveals a very distinct laminar staining for each of complement factor H, vitronectin, and amyloid beta on the outer surface of the HAP spherules (FIGS. 2d, 2e, and 2f, respectively). Not all HAP spherules are positive for these individual proteins, suggesting a heterogeneity within sub-RPE deposits, possibly reflecting localised events, such as site-specific secretory events or highly localised inflammatory reactions. In some cases HAP spherules are present where no discernable deposit has formed (FIG. 2c), suggesting that HAP spherule formation precedes deposition of proteins. Osteoblasts have not, been observed in the retina, suggesting that the HAP deposition process in between the RPE and the Bruch's membrane differs fundamentally from that in bone and teeth.

Surrounding tissues contribute to sub-RPE deposit formation. Given the presence of several proteins from RPE in drusen, it was tested whether HAP is indeed capable of binding proteins secreted by RPE in vitro. Thus, a high-throughput quantitative proteomic analysis was carried out on secreted proteins bound to extracellular HAP-coated beads: ARPE-19 cells, a widely used cell model for RPE studies, were cultured with stable isotope-labelled amino acids (SILAC) to allow in vivo incorporation of a label into proteins for mass spectrometry (MS)-based quantitative proteomic analysis. SILAC-MS was used to unambiguously identify the secreted proteins binding to HAP and rank them based on their apparent affinities under the experimental conditions. In total, proteins were quantified in the eluates of the HAP beads, and were significantly enriched in the HAP-coated micro spherules compared to the carrier beads only (negative control). Amongst these were several other drusen proteins that had been identified. Complement factor H, which had been shown to be produced and secreted by RPE cells and whose Y402H variant is a genetic risk factor for AMD, exhibited nearly the highest affinity HAP binding. The high affinity binding of CFH to HAP supports the finding of the immunohistochemical co-localisation of these two sub-RPE deposit components.

Figure 3:
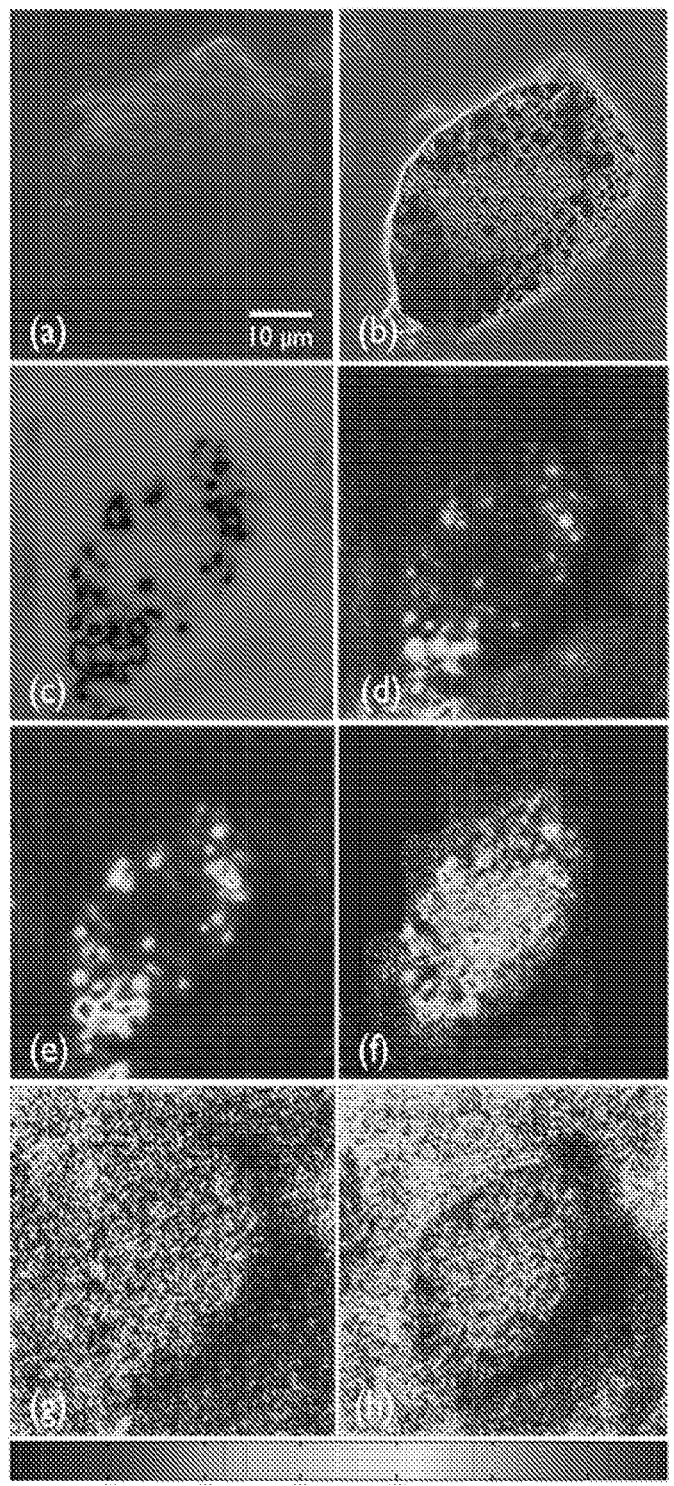
FIG. 3 includes scanning secondary electron images showing a druse before (a) and after (b) focused ion beam (FIB) milling, a non-negative matrix factorisation score plot showing chemically distinct spherules inside the druse (c), and also includes positive ion secondary ion mass spectrometry (SIMS) images showing calcium (d), calcium phosphate (e), cholesterol (f), phosphatidylcholine headgroup (g), and combined signals from characteristic protein fragments (h).
Figure 8:
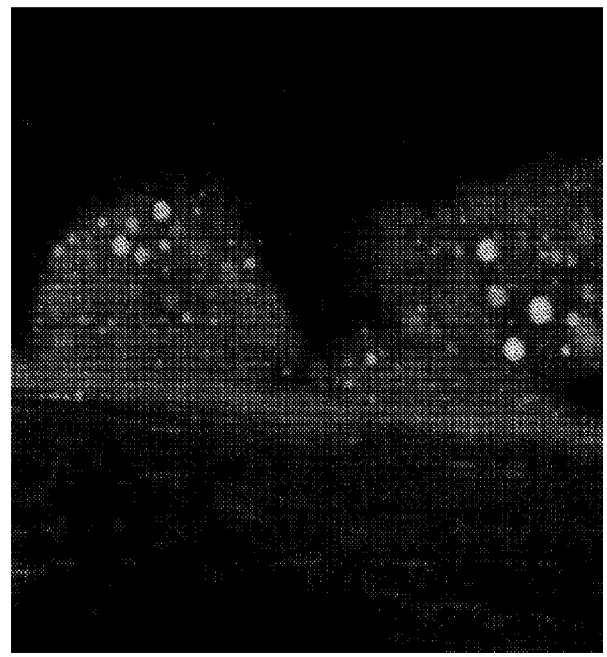
FIG. 8 includes an image of nile red staining of neutral lipids in a flat mounted RPE/choroid complex showing different sized neutral lipid spherules in the drusen at excitation 540 nm, emission 640 nm.

Without being bound by theory or mechanism, HAP may form on the surface of an existing structure at the RPE/BM interface, for example lipid droplets or lipoproteins. Lipids are known to be actively transported through the BM and therefore could potentially provide the scaffold for HAP formation. Lipid or cholesterol micelles can be coated by HAP in vivo, but it seems unlikely that HAP would only form on the much smaller (<200 nm) lipoprotein particles reportedly present in BM. To attempt to visualize lipids that might be present in the centers of the spherules, unfixed whole mount samples with visible drusen deposits on Bruch's membrane were stained with Nile Red, a fluorescent dye for neutral lipids. Nile Red labelled a large number of spherical inclusions in these samples, reminescent of HAP spherules on optical cross sections (FIG. 8). Unfortunately, double labeling with Nile Red and the HAP dyes was unsuccessful due to incompatibilities of the reagents. The composition of the inner core of HAP spherules was analyzed by mass spectrometric imaging (FIG. 3). For this experiment, drusen identified on freshly dissected, flat mounted and freeze dried BM, were (FIG. 3a) first milled using a focused ion beam (FIB). This revealed the inner structure without the need for fixation and sectioning (FIG. 3b) that could have interfered with the chemical composition inside drusen. The native chemical composition was then analysed with time-of-flight secondary ion mass spectrometry (TOF-SIMS), which is well suited, as it combines high lateral resolution (~250 nm) and very high sensitivity in the range of parts per million, and can image molecular ions and organic molecules over a wide mass range. This analysis provided detailed and independent maps of calcium (FIG. 3d), Ca-phosphate (FIG. 3e) and organic molecules such as cholesterol (FIG. 3f), an ion characteristic of phosphatidylcholine (FIG. 3g), and overall protein signature (FIG. 3h). The experiments demonstrated that the spherule shells in drusen are associated with calcium and calcium-phosphate signals, and revealed that they are also associated with cholesterol in the core, but not phospholipids. The m/e 184 ion (i.e. from the phosphocholine headgroup fragment from phospholipids) is readily detected by TOF-SIMS as a characteristic marker, so its absence from the spherules implies a strong predominance of cholesterol and/or cholesteryl esters within the spherules.

Figure 4:
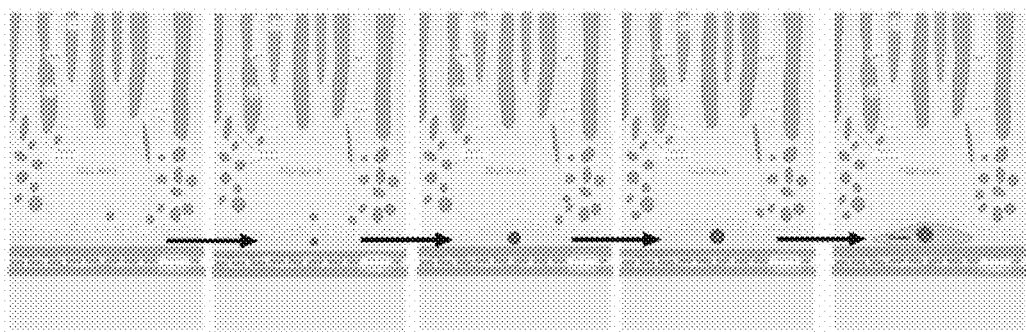
FIG. 4 includes a schematic diagram of the initiation of sub-RPE deposit formation showing the deposition of HAP onto lipid (cholesterol) droplets (a-c), followed by protein binding to the HAP surface (d), which facilitates further deposition to form the visible deposit (e).

Without being bound by theory or mechansim, it appears from these observations that sub-RPE deposits are formed, at least partly, due to the deposition of HAP shells on cholesterol-containing droplets present at the RPE/choroid interface. Once the HAP-coated spherules are formed they have the capacity to bind proteins, forming nucleation sites for sub-RPE deposit formation. These structures may promote binding of other proteins and lipids, leading to a self-driven oligomerisation process and the growth of sub-RPE deposits (FIG. 4). Characterizing how the HAP shells form, how proteins bind to their surfaces, and how this promotes the formation of the sub-RPE deposits allows strategies to detect the formation of deposits at an early stage, well before sight-threatening conditions develop.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a label" includes a plurality of such labels, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references, including those listed below, are incorporated herein by reference.

REFERENCES

1. Lim, L. S., Mitchell, P., Seddon, J. M., Holz, F. G. & Wong, T. Y. Age-related macular degeneration. *The Lancet* 379, 1728-1738 (2012).
2. Wong, T. Y., Li, X., Su, X., Cheung, G. C. & Cheng, C.-Y. in *Invest. Ophthalmol. Vis. Sci.* Vol. 54 738-(2013).
3. Sarks, S. H. Ageing and degeneration in the macular region: a clinico-pathological study. *The British journal of ophthalmology* 60, 324-341 (1976).
4. Sarks, S. H., Arnold, J. J., Killingsworth, M. C. & Sarks, J. P. Early drusen formation in the normal and aging eye and their relation to age related maculopathy: a clinicopathological study. *The British journal of ophthalmology* 83, 358-368 (1999).
5. Pauleikhoff, D., Harper, C. A., Marshall, J. & Bird, A. C. Aging changes in Bruch's membrane. A histochemical and morphologic study. *Ophthalmology* 97, 171-178 (1990).
6. Pauleikhoff, D., Barondes, M. J., Minassian, D., Chisholm, I. H. & Bird, A. C. Drusen as risk factors in age-related macular disease. *American journal of ophthalmology* 109, 38-43 (1990).
7. Moore, D. J., Hussain, A. A. & Marshall, J. Age-related variation in the hydraulic conductivity of Bruch's membrane. *Investigative ophthalmology & visual science* 36, 1290-1297 (1995).
8. Lengyel, I. et al. Association of drusen deposition with choroidal intercapillary pillars in the aging human eye. *Invest Ophthalmol Vis Sci* 45, 2886-2892 (2004).
9. Hussain, A. A., Starita, C., Hodgetts, A. & Marshall, J. Macromolecular diffusion characteristics of ageing human Bruch's membrane: implications for age-related macular degeneration (AMD). *Experimental eye research* 90, 703-710, doi:10.1016/j.exer.2010.02.013 (2010).
10. Bhutto, I. & Lutty, G. Understanding age-related macular degeneration (AMD): Relationships between the photoreceptor/retinal pigment epithelium/Bruch's membrane/choriocapillaris complex. *Molecular Aspects of Medicine* 33, 295-317, doi:10.1016/j.mam.2012.04.005 (2012).
11. Curcio, C. A., Johnson, M., Rudolf, M. & Huang, J. D. The oil spill in ageing Bruch membrane. *The British journal of ophthalmology*, doi:10.1136/bjophthalmol-2011-300344 (2011).
12. Hollyfield, J. G. Age-related macular degeneration: the molecular link between oxidative damage, tissue-specific inflammation and outer retinal disease: the Proctor lecture. *Investigative ophthalmology & visual science* 51, 1275-1281, doi:10.1167/iovs.09-4478 (2010).
13. Lengyel, I. et al. High concentration of zinc in sub-retinal pigment epithelial deposits. *Exp Eye Res* 84, 772-780 (2007).
14. Giachelli, C. M. Ectopic calcification: gathering hard facts about soft tissue mineralization. *The American journal of pathology* 154, 671-675, doi:10.1016/S0002-9440(10)65313-8 (1999).
15. Davis, W. L., Jones, R. G. & Hagler, H. K. An electron microscopic histochemical and analytical X-ray microprobe study of calcification in Bruch's membrane from human eyes. *The journal of histochemistry and cytochemistry: official journal of the Histochemistry Society* 29, 601-608 (1981).
16. Vogt, S. D. et al. Retinal pigment epithelial expression of complement regulator CD46 is altered early in the course of geographic atrophy. *Experimental eye research* 93, 413-423, doi:10.1016/j.exer.2011.06.002 (2011).
17. Raggatt, L. J. & Partridge, N. C. Cellular and molecular mechanisms of bone remodeling. *The Journal of biological chemistry* 285, 25103-25108, doi:10.1074/jbc.R109.041087 (2010).
18. Skinner, H. C. & Nalbandian, J. Tetracyclines and mineralized tissues: review and perspectives. *Yale J Biol Med* 48, 377-397 (1975).
19. Kovar, J. L. et al. Near-infrared-labeled tetracycline derivative is an effective marker of bone deposition in mice. *Anal Biochem* 416, 167-173, doi:10.1016/j.ab.2011.05.011 (2011).
20. Vilmann, H. The in vivo staining of bone with alizarin red S. *J Anat* 105, 533-545 (1969).
21. Rahn, B. A. & Perren, S. M. Xylenol orange, a fluorochrome useful in polychrome sequential labeling of calcifying tissues. *Stain Technol* 46, 125-129 (1971).
22. Johnson, L. V. et al. The Alzheimer's A beta-peptide is deposited at sites of complement activation in pathologic deposits associated with aging and age-related macular degeneration. *Proc Natl Acad Sci USA* 99, 11830-11835 (2002).
23. Dentchev, T., Milam, A. H., Lee, V. M., Trojanowski, J. Q. & Dunaief, J. L. Amyloid-beta is found in drusen from some age-related macular degeneration retinas, but not in drusen from normal retinas. *Mol Vis* 9, 184-190 (2003).
24. Anderson, D. H. et al. Characterization of beta amyloid assemblies in drusen: the deposits associated with aging and age-related macular degeneration. *Exp Eye Res* 78, 243-256 (2004).
25. Ohno-Matsui, K. Parallel findings in age-related macular degeneration and Alzheimer's disease. *Progress in retinal and eye research* 30, 217-238, doi:10.1016/j.preteyeres.2011.02.004 (2011).
26. Hageman, G. S. et al. A common haplotype in the complement regulatory gene factor H (HF1/CFH) predisposes individuals to age-related macular degeneration. *Proc Natl Acad Sci USA* 102, 7227-7232 (2005).
27. Mullins, R. F., Russell, S. R., Anderson, D. H. & Hageman, G. S. Drusen associated with aging and age-related macular degeneration contain proteins common to extracellular deposits associated with atherosclerosis, elastosis, amyloidosis, and dense deposit disease. *Faseb J* 14, 835-846 (2000).
28. Hageman, G. S., Mullins, R. F., Russell, S. R., Johnson, L. V. & Anderson, D. H. Vitronectin is a constituent of ocular drusen and the vitronectin gene is expressed in human retinal pigmented epithelial cells. *Faseb J* 13, 477-484 (1999).
29. Hageman, G. S. & Mullins, R. F. Molecular composition of drusen as related to substructural phenotype. *Mol Vis* 5, 28 (1999).
30. Hjerten, S., Levin, O. & Tiselius, A. Protein chromatography on calcium phosphate columns. *Archives of biochemistry and biophysics* 65, 132-155 (1956).
31. Porath, J. Some Recent Developments in Preparative Electrophoresis and Gel Filtration. *Metabolism* 13, SUPPL:1004-1015 (1964).
32. Cummings, L. J., Snyder, M. A. & Brisack, K. in *Methods Enzymol* Vol. Volume 463 (eds R. Burgess Richard & P. Deutscher Murray) 387-404 (Academic Press, 2009).
33. Russell, S. R., Mullins, R. F., Schneider, B. L. & Hageman, G. S. Location, substructure, and composition of basal laminar drusen compared with drusen associated with aging and age-related macular degeneration. *American journal of ophthalmology* 129, 205-214 (2000).
34. Curcio, C. A., Millican, C. L., Bailey, T. & Kruth, H. S. Accumulation of cholesterol with age in human Bruch's membrane. *Invest Ophthalmol Vis Sci* 42, 265-274 (2001).
35. Farkas, T. G., Sylvester, V. & Archer, D. The ultrastructure of drusen. *American journal of ophthalmology* 71, 1196-1205 (1971).
36. Crabb, J. W. et al. Drusen proteome analysis: an approach to the etiology of age-related macular degeneration. *Proc Natl Acad Sci USA* 99, 14682-14687 (2002).
37. Hou, Y., Morrison, C. J. & Cramer, S. M. Classification of protein binding in hydroxyapatite chromatography: synergistic interactions on the molecular scale. *Anal Chem* 83, 3709-3716, doi:10.1021/ac103336h (2011).

38. Chen, M., Forrester, J. V. & Xu, H. Synthesis of complement factor H by retinal pigment epithelial cells is down-regulated by oxidized photoreceptor outer segments. *Exp Eye Res* 84, 635-645 (2007).
39. Edwards, A. O. et al. Complement factor H polymorphism and age-related macular degeneration. *Science* 308, 421-424 (2005).
40. Klein, R. J. et al. Complement factor H polymorphism in age-related macular degeneration. *Science* 308, 385-389 (2005).
41. Holz, F. G., Sheraidah, G., Pauleikhoff, D. & Bird, A. C. Analysis of lipid deposits extracted from human macular and peripheral Bruch's membrane. *Arch Ophthalmol* 112, 402-406 (1994).
42. Mullins, R. F. & Hageman, G. S. Human ocular drusen possess novel core domains with a distinct carbohydrate composition. *J Histochem Cytochem* 47, 1533-1540 (1999).
43. Raggio, C. L., Boyan, B. D. & Boskey, A. L. In vivo hydroxyapatite formation induced by lipids. *J Bone Miner Res* 1, 409-415, doi:10.1002/jbmr.5650010505 (1986).
44. Curcio, C. A., Johnson, M., Huang, J. D. & Rudolf, M. Apolipoprotein B-containing lipoproteins in retinal aging and age-related macular degeneration. *Journal of lipid research* 51, 451-467, doi:10.1194/jlr.R002238 (2010).
45. Fletcher, J. S. & Vickerman, J. C. Secondary ion mass spectrometry: characterizing complex samples in two and three dimensions. *Anal Chem* 85, 610-639, doi:10.1021/ac303088m (2013).
46. Pecorella, I., Ciardi, A., Scardino, A., Marasco, A. & Di Tondo, U. A scanning transmission microscopy and energy-dispersive X-ray microanalysis of idiopathic ocular calcification and oxalosis in AIDS patients. *Ultrastruct Pathol* 23, 223-231 (1999).
47. Spraul, C. W. & Grossniklaus, H. E. Characteristics of Drusen and Bruch's membrane in postmortem eyes with age-related macular degeneration. *Archives of ophthalmology* 115, 267-273 (1997).
48. Ulshafer, R. J., Allen, C. B., Nicolaissen, B., Jr. & Rubin, M. L. Scanning electron microscopy of human drusen. *Investigative ophthalmology & visual science* 28, 683-689 (1987).
49. Ulshafer, R. J., Allen, C. B. & Rubin, M. L. Distributions of elements in the human retinal pigment epithelium. *Archives of ophthalmology* 108, 113-117 (1990).
50. van der Schaft, T. L., de Bruijn, W. C., Mooy, C. M., Ketelaars, D. A. & de Jong, P. T. Element analysis of the early stages of age-related macular degeneration. *Archives of ophthalmology* 110, 389-394 (1992).
51. Boskey, A. L. & Posner, A. S. Formation of hydroxyapatite at low supersaturation. *The Journal of Physical Chemistry* 80, 40-45, doi:10.1021/j100542a009 (1976).
52. Haimovici, R., Gantz, D. L., Rumelt, S., Freddo, T. F. & Small, D. M. The lipid composition of drusen, Bruch's membrane, and sclera by hot stage polarizing light microscopy. *Invest Ophthalmol Vis Sci* 42, 1592-1599 (2001).
53. Curcio, C. A. et al. Esterified and unesterified cholesterol in drusen and basal deposits of eyes with age-related maculopathy. *Exp Eye Res* 81, 731-741 (2005).
54. Li, C. M. et al. Lipoprotein-like particles and cholesteryl esters in human Bruch's membrane: initial characterization. *Invest Ophthalmol Vis Sci* 46, 2576-2586 (2005).
55. Bendall, S. C. et al. Prevention of amino acid conversion in SILAC experiments with embryonic stem cells. *Mol Cell Proteomics* 7, 1587-1597, doi:10.1074/mcp.M800113-MCP200 (2008).
56. Gloeckner, C. J., Boldt, K. & Ueffing, M. in *Current Protocols in Protein Science* (John Wiley & Sons, Inc., 2001).
57. Hammersley, A. P. ESRF98HA01T, FIT2D V9.129 Reference Manual V3.1. (1998).

We claim:

1. A method for obtaining a profile of hydroxyapatite (HAP) deposits in an eye of a subject, comprising:
   administering to the eye of the subject a HAP label compound comprising a HAP binding moiety and a label moiety; and
   obtaining a profile of HAP deposits in the eye of the subject, wherein obtaining a profile of HAP deposits in the subject comprises scanning the retina of the subject for labeled HAP deposits.

2. The method according to claim 1, further comprising the step of generating an image based on scanned labeled HAP deposits.

3. The method according to claim 1, further comprising providing a reference profile of HAP deposits, wherein the reference profile is a profile expected to be seen at a particular stage of age-related macular degeneration.

4. The method according to claim 1, further comprising administering to the subject a treatment for age-related macular degeneration when the profile of deposits in the subject is associated with age-related macular degeneration.

5. The method according to claim 1, wherein the HAP label compound comprises the HAP binding moiety conjugated to the label moiety, and wherein the label moiety is a signal generating moiety that is capable of producing a detectable signal.

6. The method according to claim 5, wherein the HAP binding moiety is selected from the group consisting of tetracycline derivatives, xylenol orange, alizarin red, calcein, phosphonates, pamidronate, bis-iminodiacetates, HAP-binding peptides, and combinations thereof.

7. The method according to claim 5, wherein the detectable signal is fluorescence.

8. The method according to claim 5, wherein the signal generating moiety is a fluorescent label moiety.

9. The method according to claim 5, wherein the signal generating moiety includes an emission spectrum in the visible range, near infrared range, infrared range, or combinations thereof.

10. The method according to claim 5, wherein the signal generating moiety includes an excitation spectrum in the visible range, near infrared range, infrared range, or combinations thereof.

11. The method according to claim 1, further comprising predicting or diagnosing age-related macular degeneration when HAP deposits are identified in the retina of the subject.

12. A method for labeling or detecting HAP deposits in an eye, comprising:
    contacting a HAP label comprising a HAP binding moiety and a signal generating moiety with a tissue sample of the eye; and
    detecting a signal from the HAP label.

13. The method according to claim 12, wherein the contacting step includes administering eye drops comprising the HAP label to an eye of a subject.

14. The method according to claim 12, wherein the step of contacting includes contacting a retina of a subject with the HAP label.

15. The method according to claim 12, wherein the contacting step includes injecting the HAP label into a vitreous humor of an eye of a subject.

16. The method according to claim 12, wherein the HAP label comprises a HAP binding moiety selected from the group consisting of tetracycline or derivatives thereof, xylenol orange, and alizarin red.

17. The method according to claim 12, wherein the signal generating moiety comprises a fluorescent label moiety including an emission spectrum in the visible range, near infrared range, infrared range, or combinations thereof.

18. The method according to claim 17, wherein the emission spectrum includes a peak wavelength of between about 450 nm and about 1800 nm.

19. The method according to claim 12, wherein the signal generating moiety comprises a fluorescent label moiety including an excitation spectrum in the visible range, near infrared range, infrared range, or combinations thereof.

20. The method according to claim 12, wherein the HAP label comprises a HAP binding moiety, which may or may not be capable of producing a detectable signal, conjugated to a signal generating moiety, which is capable of producing a detectable signal.

21. The method according to claim 12, wherein the HAP label exhibits a change in detectable signal upon binding to HAP.

\* \* \* \* \*